(12) United States Patent
Kamei

(10) Patent No.: US 6,537,301 B1
(45) Date of Patent: Mar. 25, 2003

(54) METHOD OF NONINVASIVELY ENHANCING IMMUNOSURVEILLANCE CAPACITY AND APPARATUS FOR APPLYING PULSED LIGHT TO AT LEAST FOREHEAD

(76) Inventor: Tsutomu Kamei, 681-3 Matsuyorishimo-cho, Izumo-shi, Shimane (JP)

( * ) Notice: Subject to any disclaimer, the term of this patent is extended or adjusted under 35 U.S.C. 154(b) by 0 days.

(21) Appl. No.: 09/546,327

(22) Filed: Apr. 10, 2000

Related U.S. Application Data

(62) Division of application No. 09/002,486, filed on Jan. 2, 1998, which is a division of application No. 08/620,278, filed on Mar. 22, 1996, now Pat. No. 5,769,878.

(30) Foreign Application Priority Data

Mar. 23, 1995 (JP) ................................................ 7-91270

(51) Int. Cl.⁷ ................................................ A61B 5/06
(52) U.S. Cl. ....................................................... 607/88
(58) Field of Search ................................ 600/544–546, 600/26–28, 322, 323, 340, 344; 607/88–90, 93; 362/103–107, 257–261, 263, 457, 458, 804; 602/2

(56) References Cited

U.S. PATENT DOCUMENTS

| | | | |
|---|---|---|---|
| 4,044,756 A | * | 8/1977 | Hamilton et al. ............... 128/2 |
| 4,315,502 A | | 2/1982 | Gorges |
| 4,665,926 A | | 5/1987 | Leuner et al. |
| 5,047,006 A | | 9/1991 | Brandston et al. |
| 5,092,669 A | | 3/1992 | Anderson |
| 5,119,815 A | * | 6/1992 | Chance ......................... 128/633 |
| 5,241,967 A | | 9/1993 | Yasushi et al. |
| 5,265,598 A | | 11/1993 | Searfoss et al. |
| 5,403,261 A | | 4/1995 | Shimizu et al. |
| 5,409,445 A | | 4/1995 | Rubins |
| 5,409,482 A | | 4/1995 | Diamantopoulos |
| 5,495,853 A | | 3/1996 | Yasushi |
| 5,518,497 A | | 5/1996 | Widjaja et al. |
| 5,616,140 A | | 4/1997 | Prescott |
| 5,755,752 A | | 5/1998 | Segal |
| 5,849,026 A | | 12/1998 | Zhou et al. |
| 6,129,748 A | * | 10/2000 | Kamei ........................... 607/88 |

FOREIGN PATENT DOCUMENTS

| | | |
|---|---|---|
| EP | 0412629 A | 2/1991 |
| EP | 0638282 A | 2/1995 |
| WO | WO 8810091 | 12/1988 |

* cited by examiner

Primary Examiner—Michael Peffley
Assistant Examiner—Peter J Vrettakos
(74) Attorney, Agent, or Firm—McDermott, Will & Emery

(57) ABSTRACT

The invention provides a method and an apparatus for enhancing immunosurveillance capacity, particularly, NK cell activity, without administration of medicines or immunological therapy, through noninvasive and simple method. The invention provides also a method and an apparatus for enhancing power of concentration of users in intellectual activities.

The method according to the invention is carried out by applying to the forehead, with foreign lights being excluded, pulsed light in the frequency range of from 0.5 to 13 Hz, preferably in a frequency of a representative value in alpha wave band obtained by measuring brain waves of users or any frequencies near that representative value. NK cell activity is surely enhanced by the pulsed-light application with the eyes of users being shielded.

The apparatus according to the invention comprises a fitting device detachably fit onto the head or forehead of users, a light emitting means for applying pulsed light in the frequency range of alpha waves to the forehead of users, electrodes for measuring brain waves and an adjusting means for adjusting frequencies of pulsed light.

9 Claims, 15 Drawing Sheets

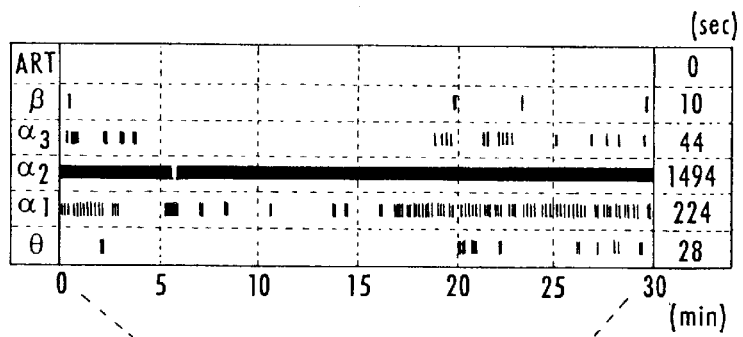
Fig. 4(a)(i)
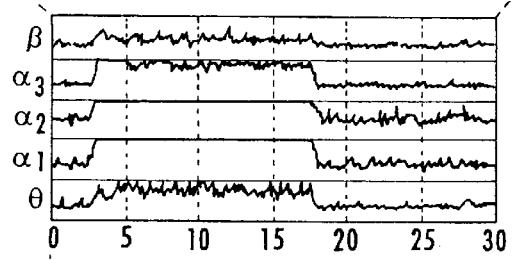
Fig. 4(a)(ii)
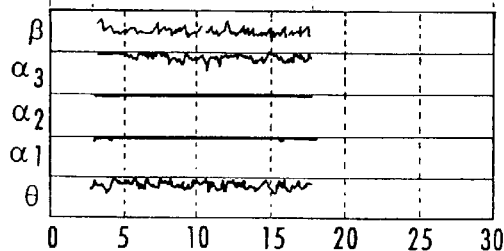
Fig. 4(a)(iii)
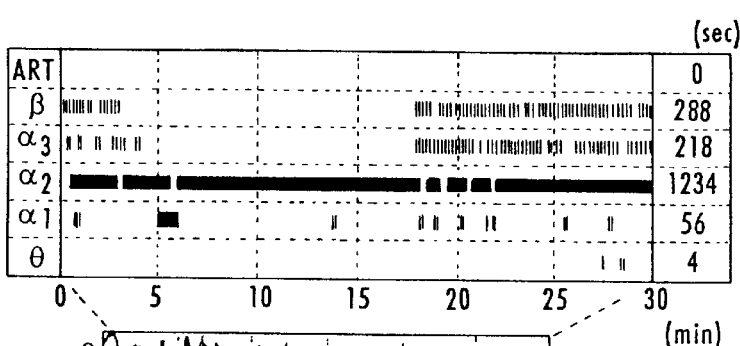
Fig. 4(b)(i)
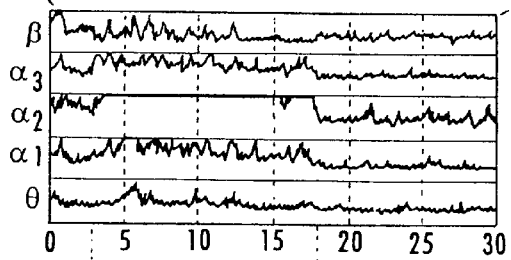
Fig. 4(b)(ii)
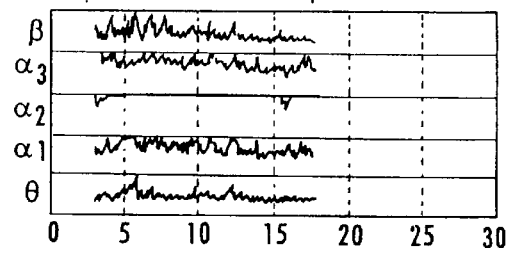
Fig. 4(b)(iii)

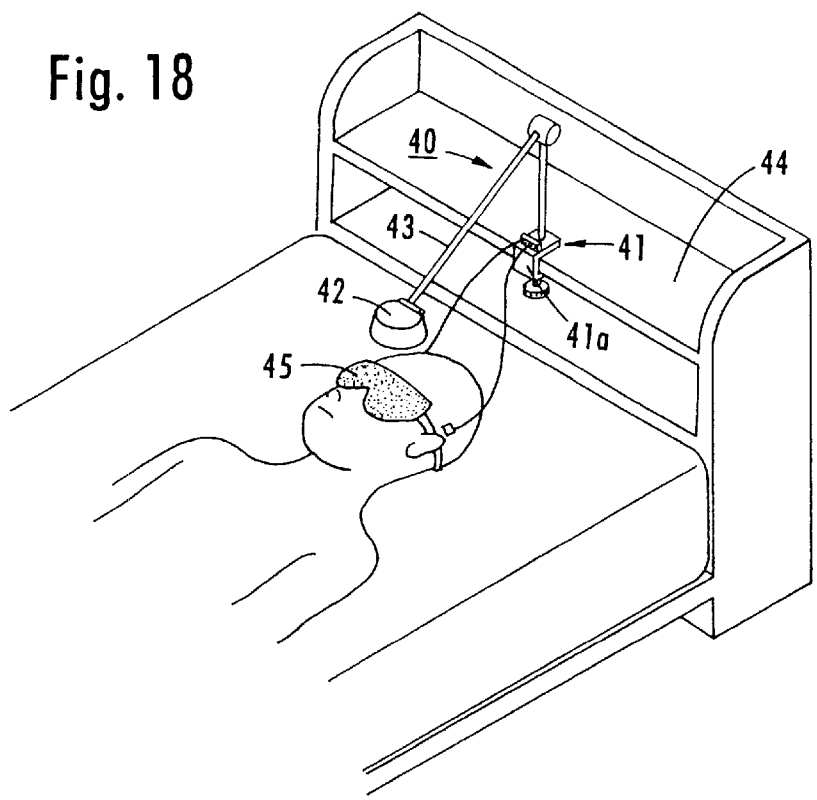
Fig. 18
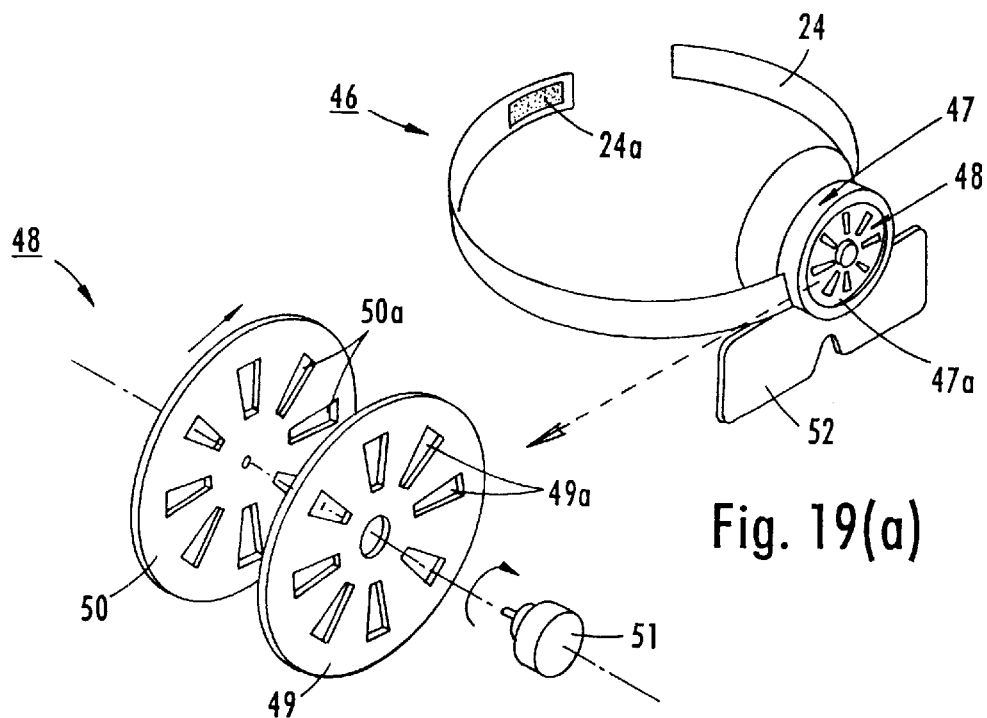
Fig. 19(a)
Fig. 19(b)

METHOD OF NONINVASIVELY ENHANCING IMMUNOSURVEILLANCE CAPACITY AND APPARATUS FOR APPLYING PULSED LIGHT TO AT LEAST FOREHEAD

This application is a divisional of application Ser. No. 09/002,486 filed Jan. 2, 1998, which is a divisional of application Ser. No. 08/620,278 filed Mar. 22 1996 now U.S. Pat. No. 5,769,878.

BACKGROUND OF THE INVENTION

The present invention relates to a method of noninvasively enhancing immunosurveillance capacity and an apparatus for applying pulsed light to forehead for realizing the method, and more particularly to a method using a noninvasive means such as applying pulsed light having frequency in the range of 0.5–1.3 Hz, preferably 8–13 Hz, to the forehead or the head including the forehead of a user to enhance the immunosurveillance capacity and also power of concentration, and an apparatus therefor.

It is hitherto known that cell-medated immunity, particularly, NK cell (natural killer cell) activity readily lowers due to mental or physical stress and the lowering of the cell-medated immunity is the most important fact leading to occurrence of a tumor. Effective means for increasing the cell-medated immunity is quite few. For example, activation of NK cell may be urged by application of medicines (e.g., poly 1:C) or cytokinin (interleukin 2, etc) produced by gene engineering, but a large amount of administration of those for a long term causes NK cells to have resistance to them, and adverse effect of the medicines are not negligible.

Details of relationship between alpha (α) wave and the immunosurveillance capacity such as NK cell activity have not been clarified. But, many attempts have been made based on the fact that when mental or physical stress is low or non at all, alpha wave of brain waves increases, and the concept that increment of alpha wave leads to elimination of the mental or physical stress.

For example, for relaxation and hypnogenesis, the subject is caused to listen to sounds having a frequency in the range of alpha wave, or a pulsed light having a frequency in the range of alpha wave is applied to the eyes of the subject. Feeble electric current in various wavelengths is produced dominantly in human brain and the alpha (α) waves in a frequency range of from about 8 to 13 Hz are produced much when a human being is in a relaxed state (relaxation), leading to such principle that stimulus having the frequency in the above range is applied to a human being to induce the human being into a relaxed state, on which principle those attempts are based. It is true that alpha waves increase by a mental effect through "ZAZEN (a sitting meditation among "Zen" practice used in Buddhism school, widely known in Japanese or others)" and external stimulus from the outside of human body, such as light. Also, the alpha waves are produced much in the human brain when the human being concentrates his consciousness upon any thing, at which the produced frequency is about 10 Hz or more, slightly higher than the relaxed state (about 9 Hz or less). It is said that Beta (β) waves are prevalent in an active or excited mental state, having a frequency ranging from about 14 to 30 Hz, and brain waves generated during drowsiness and light sleep are theta (θ) waves in a frequency band ranging from about 4 to 7 Hz, and those in coma or a deep sleep being δ waves ranging from 0.4–4 Hz.

Among alpha wave stimulation means conventionally used, a simplest feature is to cause the subject to listen to sounds recorded in the recording tapes or CD (compact discs) in the frequency range of alpha waves. Also, a photic stimulus generally uses, as shown in Japanese Patent No. 1150057 and U.S. Pat. No. 43,155,002, an eyeglasses or goggles including a lamp on the periphery of lens and a pulse signal generator which outputs a lamp lighting signal to the lamp. When the pulsed light is applied to the closed eyes of user, brain waves are synchronized with the frequency of the pulsed light through the path of vision and around occipital lobe's visual area, which phenomenan or reaction is called photic driving reaction. Still another feature is as proposed in Japanese Patent Laid-Open Publication No. 03-44538 that current of a low frequency corresponding to alpha waves is applied to flow at both lateral sides of the head of the user.

The frequency output in those conventional features is fixed or constant to thereby have less effects on the user or cause the user to feel uncomfortable. In detail, the alpha waves, which are brain waves in the frequency range from 8 to 13 Hz as foregoing, differ in specific frequency bands readily produced and average of detected frequencies, depending upon each testee due to different rhythms of alpha waves inherent in each testee. Also, the same person has a subtle change in the produced frequency bands and the average of detected frequencies of alpha waves depending upon his physical condition and time in the day for testing. Hence, the stimulus based on a frequency largely differing from alpha waves inherently produced in the human body does not provide favourable effects but results in ill effects.

A proposal adopting measurement of brain waves for providing stimulus based on a representative value of alpha waves or any frequency near the same has been made to solve the above problem, as seen in Japanese Patent Laid-Open Publication No. 03-70572 wherein a goggle for inducing brain waves comprises a head band including a a light-shielding member on the user's face covering the users eyes, a light emitting part provided inside the light-shielding member, and brain wave electrodes through which brain waves signals are measured according to which light-emitting signals of the same frequency as of alpha waves are sent to a light-emitting part. The goggle is used as applying the light to the eyes of a user in a relaxed state with the eyelids covering the eyeballs. This art is called "Photic Feedback" by a kind of biological circuit including the user himself in a closed loop wherein the aimed alpha waves are induced intensively and quickly through the photic feedback, thereby bringing the user into a relaxed state quickly. The art has been published in U.S. Pat. No. 5,241, 967 (based on Japanese Patent Laid-Open Publication No. 02-168932 and other two publications).

According to the photic driving feature, the pulsed light hits the eyes even when covered by the eyelids. Hence, the stimulus prevents users from being brought into a sufficient relaxed state, and alpha waves do not increase. This problem cannot be solved by the photic feedback technique. In addition, the photic driving feature has a critical defect due to the eyes of user being covered. That is, alpha waves have function facilitating volition and power of concentration as well as hypnogenesis and relaxation. The more the power of concentration is increased, the higher the efficiency of metal activities such as reading, learning, studying or literary work becomes. It is impossible to do such working with the eyes being covered.

Similarly, sounds in the frequency range of alpha waves hinder the reading, learning, studying or thinking, and the monotonous sounds may irritate users. In the meantime, another conventional feature causing current of the low frequency to flow in brain of user results in disturbing brain wave itself. Use of this feature is dangerous even using a feeble current and prefeably requires controlling by doctors. That is, the feature is not readily usable by ordinary persons.

The inventor zealourshy studied to solve those problems and obtained the results as follows. The inventor applied the pulsed light not to the eyes of users but to the forehead placed above the eyes and found the phenomenon that alpha wave component of brain waves extracted through the forehead increased, and the user was brought into a quite favourable relaxed state and had an increased power of concentration. This is inferably because the forehead, which is the center of volition, will and language or speech, was activated by increment of alpha waves, particularly, in the frequency range of about 10 Hz or more. Also, such phenomenon was surprisingly found that immunological activity (NK cell activity) of the testee increased during and for a while after application of the pulsed light. Such phenomenon had not been known at all and was found first by the inventor.

The method according to the present invention has been achieved based on the results of experiments for proving that phenomenon, and the apparatus for applying pulsed light to forehead according to the present invention has been achieved as a means for embodying the method. Next, the present invention will be detailed with referring to the experiments.

The method according to the present invention enhances the immunosurveillance capacity and power of concentration of users by applying to the forehead or the head including the forehead of the users a pulsed light having a frequency particularly in the range of alpha waves. The immunosurveillance capacity is an immunologically surveying function to distinguish a newly produced aberrant cells, such as malignant cells (cancerous cells), including a new antigen generated by mutation of somatic cells, and reacts on (i.e., rapid breaking) the aberrant cells. Cells behaving the immunosurveillance are macropharge, B cells, Killer T cells and NK cells.

NK cells (natural killer cells) does, from the birth of the persons and without necessity of sentitization against antigen, distinguish cells infected with virus and cancerous cells and give to those cells activity of breaking themselves. The NK cells are immunocyte fulfilling most important duties in immunosurveillance for prevention of carcinogenesis. Also, NK cells serve as defense cells at local areas of dissemination in the so-called metastasis wherein cancerated cells disseminate from a focus hematogenically and lymphatically. Hence, improvement of activity of NK cells is very much important for prevention and cure of cancer. In this regard, the application of pulsed light in the frequency range of alpha waves to the forehead of users should be quite significant.

It has been reported that NK cell activity can be enhanced by administration of virus and BCG and increased by interferon, interleukin 2, etc. According to the present invention, NK cell activity can be enhanced not by administration of medicines, so that there is no fear of adverse effect by the medicines. Although lowering of noradrenaline among catecholamine (naming generically adrenaline, noradrenaline and dopamine) was observed in application of a pulsed light to the forehead of user, no change was seen in adrenaline, dopamine and β-endorphin. Also, users did not feel uncomfortable in application of the pulsed light to their foreheads. In these respects, there is no fear of adverse effect by application of pulsed light to the forehead.

The "forehead" referred to in the invention means the part of face placed above the eyes, i.e., the so-called forehead and the area near the same including the middle of the forehead (exclusive of the eyes and other parts placed below the forehead), and also includes the case of application of pulsed light to the "head" including the forehead as well as the case of application to the forehead. (The "head" referred to in the invention means the part placed above the eyes, excluding the eyes and other parts placed below the forehead) Specific mechanism of enhancement of NK cell activity caused by applying pulsed light to the forehead has not been clarified. But, it is said that sensory organ of conarium exists in the forehead, and it is inferred that conarium is stimulated by the applied pulsed light through the sensory organ, although a location of the sensory organ has not been specified. Hence, the target of applying the pulsed light may be the area of a part of the forehead about 5–10 cm in diameter including the middle of the forehead.

The pulsed light referred to in the invention is a periodic intermittent light. Pulse referred to in the electric art means voltage and current having waveforms other than sine wave and generally means square wave. Time from rise of a wave to rise of a next wave is called a period (T) and an inverse number of the period f=1/T is called a repeated frequency. The frequency of pulsed light in the present invention is the repeated frequency. The pulsed light of the invention includes stroboscopic light and a light provided by intermittently shutting sunlight and a general lighting beam. Such pulsed light when applied to the forehead and the head serves as a kind of photic stimulus.

The method according to the present invention does not exclude that the pulsed light is applied to the eyes. The pulsed light even when applied to both of the forehead and eyes provides tendency of enhancement of NK cell activity. But, the pulsed light when applied only to the eyes did not have a result of a significant difference in enhancement of NK cell activity and there was observed a tendency of lowering of that enhancement depending upon specific users, on which any reasons have not been found. By contrary, the pulsed light when applied to the forehead with the eyes being shielded showed a significant enhancement of NK cell activity. Thus, for the purpose of enhancing NK cell activity, the eyes are prefeably to be shielded upon application of the pulsed light to the forehead. In the above two cases of applying the pulsed light to the eyes, alpha waves increased largely particularly at the occipital region together with amplification of amplitude. By contrary, upon application of pulsed light with the eyes being shield, alpha waves increased only at the forehead. Since the forehead is the center of volition, will and language, application only to the forehead is enough to increase power of concentration.

Application of pulsed light in the invention may use any methods by which the light can be applied to the forehead and the head including the forehead, such as that a fitting device having a light emitting means is fit on the head of users, that users may place the forehead near an electric stand having a source of pulsed light, or that a fitting device provided with a shutter intermittently shutting sunlight or an illuminating light is fit onto the head of users to cause pulsed sunlight or illuminating light to be applied to the forehead. Applying the pulsed light is preferably to be carried out with the forehead being completely or substantially not applied with foreign lights and with the users being in a relaxed state.

Frequencies of the pulsed light is in the range of 0.5–13 Hz and preferably 8–13 Hz as of alpha waves. 14–30 Hz, the range of beta waves is not preferable due to causing excitation. Other frequencies such as theta waves and delta waves in the range of less than 8 Hz also exhibit enhancement of immunosurveillance capacity and power of concentration, which is though lower than alpha alpha waves, and higher frequencies makes larger the enhancement effects. However, the frequencies when having difference from those of user's brain waves have not the enhancing effects or, contrary, lower the same. Thus, it is preferable to use a pulsed light having a frequency corresponding to a representative value of alpha waves obtained by measuring the brain wave of users or any frequencies near the representative value. Selection of the frequencies may be manually carried out, and the most preferable feature is that during application of pulsed light, brain wave signals of users are extracted to a brain wave inducing device which picks up signal components of alpha waves to calculate a representative value thereof and feeds back the representative value or any frequency near the same as a light-applying signal. According to the feature, users when use the method of the invention in their sleeping may favourably have a gradual reduction of frequency from the range of alpha waves upon going to bed to the theta wave range in sleeping, and be not subject to physiological pressure.

The invention uses LED as a light source for the pulsed light since LED is small in size, lightweight to be readily applicable, but the light source should not be limitted to LED and may employ any artificial light sources radiating visible light beams or infrared, such as a tungsten-filament lamp, etc. Illuminance of 30–50 lux showed a sufficient effect. Sunlight or illuminating light may be also applicable wherein a fitting device provided with a shutter intermittently shutting sunlight or illuminating light is fit onto the head to cause pulsed sunlight or illuminating light to be applied to the forehead of users.

Next, the experiments and results will be detailed.
(Experiment A)
Apparatus for Experiment A photo-feedback device (called hereunder PFB device, RELACTIVE 1: Pioneer Electronic Corporation) for mental relaxation was used in the following manner. The PFB device comprises an easy-chair for the testee, a band type electrode to be fit on the head of the testee (2 electrodes are retained both lateral sides of the forehead), a light source for application of light to the eyes of testee (red LED, 660 nm), and a control unit which picks up, by use of a bandpass filter having center frequency of 10.0 Hz, alpha wave components from brain waves extracted from the testee and controls in real time a frequency and amplitude of pulsed light according to the frequency and amplitude of the picked alpha wave components. Controlling the frequencies of pulsed light as above is called the photo-feedback (PFB). Also used in the experiment were a multi-channel bioamplifier (Biotop 6R12-4 (NEC San-ei Co.Ltd.) provided with a cap type electrode having 16 electrodes thereon) and an alpha wave bio-feedback device (FM515, used with sounds signals being cut: Futek Electronics Co.Ltd.). The cap type electrode was used in 1st and 21st PFB, and the band type electrode in others (Experiment A(a)).
Methods and Results of Experiments
Experiment A(a)

Subjected to experiment were testees, 13 healthy men having had no mental and physical stress, set in rest (sitting on the easy chairs inclined 30–45 degrees) with eyes not shielded against light. Illuminance of pulsed light was about 30 lux (set apart from about 10 cm). As shown in FIG. 1(a), PFB (application of pulsed light before the testees' eyes for 20 min each time) was carried out 21 times to measure brain waves each time and check change mainly in alpha wave component. Also, at the 1st and 21st PFB, the cap-type electrodes were used and blood collection was made to check change in immunosurveillance capacity. Since either the cap-type electrode or the band type electrode was fit in the experiment A(a), the forehead was covered at the upper half, so that application of pulsed light to the forehead was low.

Effective amplitude of brain wave in the frequency range of $10.0\pm0.5$ Hz produced at occipital region ($O_2$) in each testee in performance of PFB showed tendency of increase in comparison with the ordinary rest state with closed eyes immediately before 21st PFB, but did not lead to a significant change. The almost same tendency was seen among other channels. But, NK cell activity (measured with E/T ratio of 20:1) increased in 6 of the 13 testees and lowered in 7 before and after the 21st PFB, and showed tendency of increase only in the ordinary rest state with closed eyes just after the 21st PFB (FIG. 1(b)). Particularly, at blood collections D and E, statistical significance level (p) was: p<0.10.
Experiment A(b), Subjected to the experiment similar to Experiment A(a) were testees, 8 healthy men having had no mental and physical stress, with such different features as 16 dish-type electrodes in place of the cap-type and band-type electrodes were fit to the head other than the area of forehead, and the light source was changed in orientation to allow pulsed light to be applied mainly to the forehead of testees. Experimental procedure was the same as of the experiment A(a) (FIG. 1(a)) and blood collection A was omitted.

Effective amplitude of brain wave in the frequency range of average of alpha wave components $\pm0.5$ Hz produced in each testee in performance of PFB showed at the channels significantly increased in comparison with the ordinary rest state with closed eyes immediately before 21st PFB. The tendency of increase was higher at the channels on the vertex and temple in comparison with other channels as the forehead and occipital region. NK cell activity as shown in FIG. 1(c) increased in 5 of 8 testees and lowered in 3 before and after 21st PFB and showed tendency of increase (but not significant) before and after the ordinary rested states with closed eyes (20 min each time) followed by and following PFB. FIG. 1(d) shows average of the values of the testees in FIG. 1(c) and an extent of dispersion of those values (standard deviation), from which there is seen as a whole a tendency of increase of NK cell activity upon each blood collection.

In view of the experiments A(a) and (b), the inventor expected vaguely that applying pulsed light in the frequency range of alpha waves to the forehead increases NK cell activity. But, applying pulsed light to the eyes showed a large dispersion of fluctuation of NK cell activity and may occasionally have a fear of adverse effect. This is inferred as resulted from that any testees feel stress from the pulsed photic stimulus applied to the eyes. Hence, the following experiments B and C were, carried out with the eyes being shielded (but not shielded in the experiment partially).
(Experiment B)
Apparatus for Experiment This experiment employed the photo-feedback device (RELACTIVE 1: Pioneer Electronic Corporation) used in Experiment A, partially modified as illuminace of light source 50 lux (apart about 10 cm from the eyes) and orientation of mounting of light source to apply light to the center of forehead, with using 16 dish-type electrodes in place of the cap type electrode, and the rest used in the experiment A.

Method for Experiment

Subjected to the experiment similar to Experiment A were testees, 7 healthy men having had no mental and physical stress, with such features differing from Experiment A(a) as ① the eyes were shielded with eye masks, ② 16 dish-type electrodes in place of the cap-type electrode were fit to the head other than the area of forehead, and ③ the light source was changed in orientation to allow pulsed light to be applied mainly to the forehead of testees. One dish-type electrode was fit at the right side of forehead (near temple: $Fp_2$). Each PFB in the experiment was carried out 15 min as seen in FIG. 2(a) (1st and 2nd PFB) and FIG. 2(b) (21st and 22nd PFB). The 1st and 2nd PFB and the 21st and 22nd PFB were performed in such course of procedure that a short rest with eyes closed for five minutes followed by the ordinary rested state with closed eyes for 15 min are set before a first occurence of PFB (15 min) (e.g., the 1st PFB) to be carried out by the above method, followed by the further ordinary rested state with closed eyes for 15 min and further a second occurence of PFB (15 min) (e.g., the 2nd PFB) with the ordinary rested state with closed eyes for 15 min. Blood collection at the 21st and 22nd PFB was, made through a plastic needle previously locked up in ancon median skin vein for painless blood collection in the experiment. The experiments of 1st and 2nd PFB and 21st and 22nd PFB including blood collection were performed at the almost same time between 8 to 12 in the morning under the conditions such as room temperature, etc., set as the same as possible. NK cell activity was measured by use of $^{51}Cr$ and at E/T ratio of 50:1.

Results of Experiment and Observation

Change of alpha waves in 1st and 2nd PFB and 21st and 22nd PFB was observed with the multichannel bio-amplifier and there was seen no prevalent change. Standard deviation (SD) of brain waves of alpha wave component detected at right side of forehead ($Fp_2$) by use of an electroencephalograph assembled to the body of PFB device (Pioneer Electronic Corporation) was measured 3 minutes each time from start of PFB, for 9 minutes totally, and showed no change in 1st PFB but had a significant decrease in the 22nd.

Pulsed light in the frequency of 0.5 Hz was similarly applied 8 times (not shown in drawings) to the forehead of testees. Standard deviation (SD) of brain wave having alpha wave component upon the eighth application of pulsed light became slightly lower for a few minutes but did not continue very long. The values of the standard deviation were larger by 10–15% on an average than the experiment B (using about 10 Hz). It was seen that as a whole, the frequencies of brain wave having alpha wave component is more dispersive. Furthermore, a light by the same LED not adapted to be a pulsed light was continuously applied mainly to the foreheads of testees as in the experiment B. SD became lower as the above eighth application using 0.5 Hz but did not continue very long.

The alpha wave PFB device indicated so regarding 2 in 7 testees in 6th PFB and 1 in 10th–12th PFB that a large increment in amplitude of brain wave having alpha wave component, not usually shown, appeared at the forehead mainly for 15 min when the light is being applied. FIGS. 4(a) and 4(b) show data of two testees among those three. Brain waves of which two testees were measured without artifact in the experiment. Average of amplitude of $\alpha_2$ (alpha wave of 9–11 Hz) evoked at the forehead in the two testees for 15 minutes in PFB (from 3 min passed to 18 min passed after start of experiment) are 49.6 $\mu V$, 42.0 $\mu V$, and 48.2 $\mu V$, each being 3.53, 4.23, and 4.76 times, respectively in comparison with the ordinary 15 min rested state with closed eyes before the 1st PFB. An average of amplitude of $\alpha_2$ wave of an ordinary person is about 10 $\mu V$.

Those results expresses the fact that a phenomenon similar to the photic driving reaction was produced at a part of the head applied with the light (the forehead in this experiment) although the experiment was performed entirely with the eyes being shielded against the light.

The upper graph part (i) of FIG. 4(a) is a graph of appearance of prevalent brain waves of one of the above two testees in five frequency bands ($\theta$, $\alpha_1$, $\alpha_2$, $\alpha_3$, $\beta$), the graduation on the foot showing time passed and the numbers at the right side totals of time (sec) when the brain wave components were prevalent (ART was not measured). The intermediate graph part (ii) is a graph showing transition of amplitude of the brain waves in the five frequency bands. The lower graph part (iii) is a graph showing transition of amplitudes upon application of of pulsed light, taken from the graph part (ii). Tables 1(a) and 1(b) are specific amplitudes of the brain waves in the five frequency bands at a certain time. ¼ of each of the values are voltage ($\mu V$). Table 1(c) shows maximum values and average of amplitudes of brain waves in the five frequency bands in the graph part (iii). FIG. 4(b), Tables 2(a), 2(b) and 2(c) show data of the other testee. In FIG. 4, Tables 1 and 2, $\theta$ waves is brain wave component in the frequency range of from 4 to 6 Hz, $\alpha_1$ waves from 7 to 8 Hz, $\alpha_2$ waves from 9 to 11 Hz, $\alpha_3$ waves from 12 to 13 Hze and $\beta$ waves from 17 to 26 Hz.

Data was taken this time with the eyes being shielded against a light using an eye mask. The physiological phenomenon newly found is inferred to appear when the eyes being open without applying a light to the eyes. It was indicated this time the fact that when pulsed photic stimulus at a frequency and illuminance suitable just for testees in the frequency band of alpha waves and particularly by use of the PFB techniques is applied to the forehead, remarkably higher activation of brain waves having alpha wave component arises at a constant probability. Hence, when a person, who has made intellectual activities such as learning, working, etc., with his or her eyes open and is in a state that his power of concentration is still kept, starts using the apparatus according to the present invention with his eyes being still kept open, activation of alpha waves of the person is inferred to be relatively readily maintained and retained or further enhanced according to use of the apparatus.

NK cells do, from the birth of the persons and without necessity of sentitization against antigen, distinguish cells infected with virus and cancerous cells andd give to those cells activity of breaking themselves. The NK cells are immunocyte most important in immuno surveillance for prevention of carcinogenesis. FIG. 5(a) is a graph showing changes for the testees regarding NK cell activity (%) at the stages before 1st PFB, during 21st and 22nd PFB and in the rested and eyes-closed states before and after 21st and 22nd PFB. FIG. 5(b) shows average and dispersion (standard deviation) of NK cell activities of seven testees. Table 3 shows numerical values of average, freedom degree, t values and p values for and among the stages A through G in FIG. 5(b). As seen in Table 3, NK cell activity showed a significant increase by p<0.005 immediately after 21st and 22nd PFB and by p<0.0001 fifteen minutes minutes thereafter in comparison with the stage immediately before 21st and 22nd PFB.

Though not shown, similarly to the foregoing measurement of alpha waves, pulsed light in the frequency range of 0.5 Hz was applied to measure two times NK cell activity for 15 minutes each time according to FIG. 2. There was not seen a change of NK, cell activity in half of the testees, 15 min after each 15 minutes-application of light, but was seen a tendency of slight increase (about 10%) in the other half. This is from the fact that the times of application of light was smaller in comparison with the above Experiment and the quite low frequency 0.5 Hz was used. Hence, facilitation of the effect can be expected by increasing the number of times of light-application and employing pulsed light in the frequency range of theta ($\theta$) wave (about 4–8 Hz) that is said to increase in sleep. In other words, it is inferred that a pulsed light having center frequency comprising a frequency corresponding to theta waves produced in sleep of users or alpha waves in lower frequency range may be applied to provide a sufficiently favourable effect.

In the meantime, a safe method by which large increment of NK cell activity is obtained about one hour as shown in the data obtained this time has not been reported hitherto and also in the study based on using medicines. Hence, use of the method and apparatus according to the present invention is inferred to make a large contribution to prevent carcinogenesis and activation of virus-infected cells (e.g., in HIV carrier state, in latent infection with Herpes virus, etc.).

CD57×16++ in FIG. 6 and CD57×16−+ in FIG. 7 (particularly the latter) are said to show a quantitative change of manifestation of specific cell cortex marker of NK cells. In the present experiment, both of these showed increase or a tendency thereof, but the significant levels are lower to some extent in comparison with NK cell activity shown in FIG. 5. Hence, when the method according to the present invention is repeatedly used, activity per NK cell is inferred to increase, i.e., NK cells are enhanced in both of quality and quantity. Effective use as above of the method and apparatus according to the present invention is inferred to give a large significance to the clinical and preventive medicine as a safe and high effective method for improving reaction of immunity against "cells in the body to be excluded" such as cancerous cells (cell-mediated immunity). Table 4 shows numerical values of average, freedom degree, t values and p values for and among the stages A through G in FIG. 6, and Table 5 shows numerical values of average, freedom degree, t values and p values for and among the stages A through G in FIG. 7.

In addition to the above examination for immune system, catecholamine (adrenaline, noradrenaline and dopamine) and β-endorphin were examined (not shown). Noradrenaline lowered significantly (by $p<0.05$) at the stage before 21st and 22nd PFB in comparison with the stage before 1st PFB. Hence, repeated use of the method according to the present invention is inferred to facilitate relaxation of vascular smooth muscle and constriction of enteric smooth muscle to cause increase of blood flow through organ and provide favourable digestion, thereby enabling to have an effective situation for biological immunosurveillance. Also, antihypertensive function may be provided to hypertensives, etc. The others among the abovesaid items subjected to the examination did not show any change by PFB.

Experiment C (Apparatus for Experiment)

The modified PFB device in Experiment B was used in the experiment with a person.

(Method for Experiment)

Experiment was performed for a inpatient (man, 16) of right optic nerve glioma, in the stages being treated with interferon following use of anti-cancer drug before and after operation for glioma, with the eyes being not shielded/shielded against light. ① The case before the operation with the eyes not shielded (Experiment C-1) had the procedures shown in FIG. 8(a) (1st and 2nd PFB) and FIG. 8(b) (21st and 22nd PFB). ② The case after the operation with the eyes not shielded (Experiment C-2) had the procedures shown in FIG. 8(c) (1st, 2nd PFB) and FIG. 8(d) (21st, 22nd PFB). ③ The case after the operation with the eyes shielded (Experiment C-3) had the procedure shown in FIG. 8(e). The experiment C-3 which since carried out in continuation with that C-2 had no data about 1st and 2nd PFB. Each experiment performed 22 times PFB for 15 minutes each time, and changes of brain waves having alpha wave component and immunosurveillance capacity were observed in 1st and 2nd PFB and 21st and 22nd PFB (NK cell activity was measured with E/T ratio of 20:1).

(Experiment Results and Observation)

The above three experiments were performed in the order, wherein each experiment had 22 times PFB for 15 minutes each time. Upon 1st and 2nd PFB and 21st and 22nd PFB, observed by use of an alpha wave biofeedback device (used without sounds signals) were amplitudes of measured five brain wave bands (θ: 4–6 Hz, $\alpha_1$:7–8 Hz, $\alpha_2$: 9–11 Hz, $\alpha_3$: 12–13 Hz and β: 17–26 Hz) and ratio of time when the repective bands were prevalent. FIG. 9 the bar graph (sets of two bars) show results of averages of amplitudes measured and calculated on and in each 21st/22nd PFB and 15 min of each ordinary rested/closed eyes state before and after the 21st/22nd PFB in the three experiments, and ratio of time when $\alpha_3$ band was prevalent, which band $\alpha_3$ (12–13 Hz) was most likely to be activated by PFB for the testee among the five frequency bands. The hatched bar graph indicates average of amplitude ($\mu$V) of produced $\alpha_3$ of 12–13 and the hollow bar graph the ratio (%) of time (sec) when a $\alpha_3$ waves 11–13 Hz were prevail among the aforesaid five bands of brain waves. FIG. 9(a) shows Experiment C-1, FIG. 9(b) Experiment C-2 and FIG. 9(c) Experiment C-3.

As seen, activation of $\alpha_3$ by performance of PFB was more apparent in the case with the eyes being not shielded against light (Experiments C-1, C-2). But, NK cell activity simultaneously measured (shown by the bent lines in the drawings) did almost not increase in Experiment C-2, while increased in Experiment C-1 at each of two PFB stages and thereafter was kept at the level in the subsequent 15 minutes ordinary rested/eyes-closed state. By contrary, in Experiment C-3 with eyes shielded against light, NK cell activity clearly increased in 21 PFB, wherein activation of $\alpha_3$ was seen, and the subsequent 15 min ordinary rested/closedeyes state. Experiments C-2 and C-3 for this testee were carried out under the condition having many factors modifying the immunity, as being in treatment with interferon following use of anti-cancer drug after operation of the "brain tumor". Hence, it was anticipated that clear data is not necessarily provided on the brain waves and NK cell activity. But, it is inferred that in case of shielding the eyes against the light, the phenomenon corresponding to the photic driving reaction arose at the head (the forehead) applied with the light, similarly to Experiment B (and also partially feasible in Experiment C-1).

As seen from the above, even a patient of cancer under an immunologically specific condition due to administration of medicines, etc., when such patient repeatedly uses the method and apparatus according to the present invention (provided that each use may preferably be at an interval of 20–30 min or more for a better possibility), relaxation can be provided and immunological reaction against cancerous cells can be facilitated in safety. Use of the invention for a long term is expected to provide the effects as a therapy.

The inventor has developed the apparatus for applying pulsed light to forehead for realizing the method based on the foregoing results of various experiments. As explained hereunder, a first configuration of the apparatus for applying pulsed light to forehead comprises a fitting device detachably fit onto the head of user and provided with a light emitting means for applying pulsed light to the whole head of user including the forehead. The first configuration includes such feature that the fitting device itself serves as the light emitting means. The first configuration may include an adjusting means for adjusting frequencies of pulsed light, electrodes for measuring brain waves, power source and a control means for processing signals. A second configuration of the invention comprises a desk lamp type lighting device including a base (in place of the fitting device to be fit onto the head) to be put on or fixed on furniture such as a desk, chair, bed, etc., and a light emitting means connected to the base through an arm. The desk lamp type fitting device is usable by users in sitting position or face-up position and may have the pulsed light frequency adjusting means and others as referred to in the first configuraiton. Furthermore, a third configuration of the invention is the same as the first configuration as comprising a fitting device to be fit onto the head of users, but is basically different from that configuration in that sunlight or illuminating light is made use of as a light source for the pulsed light. For the purpose, the third configuration comprises the fitting device provided with a shielding means for shielding the forehead or the head including the forehead of users and with a shutter on an opening at the front side of the shielding means for intermittently shutting applied light. The third configuration may include the pulsed light frequency adjusting means and others as referred to in the first and second configurations. Next, the apparatus for applying the pulsed light to forehead mainly in the first configuration will be explained.

The fitting device may employ any kinds and structures which is tightly held on the user's head or forehead, such as a belt type, headphone type, a cap type (helmet type), etc., and is preferably to have an adjusting means for adjusting the fitting device correspondingly to the sizes of users heads to enable the fitting device to be tightly held on the users heads. The fitting device may comprise a retention member mountable to the forehead by adhesion or adsorption.

The light emitting means comprises a light source and a light emitter having the light source therein. The light source is not limited in kinds but may preferably employ LED (light emitting diode) to reduce power consumption. The light source may alternatively use visible radiation or infrared rays. The light emitting means may be fixed directly to the fitting device or connected thereto through an arm, a support plate, etc. In case the fitting device is the helmet or the retention member in adhesion or adsorption type, the fitting device itself may serve as the light emitting means or the light emitter. The light emitter may be shaped in a plate, dish or cup. In case the light source is substantially apart from the forehead, the plate-like or dish-like shaped light emitter possibly causes the light to be scattered and applied to the eyes of users. The present invention does not deny application of pulsed light to the eyes. But, when the pulsed light is applied to the eyes, the relaxation is likely to be hindered as foregoing. And particularly in reading necessitating power of concentration, application of pulsed light has to be avoided. Hence, for use of the plate-like or dish-like shaped light emitter, it is preferable to provide an eye-shielding member to prevent pulsed light from being applying to the eyes. The light emitter in a cup-like shape may be adapted at its front edge to adhere to or face near the forehead. Also, for use of the apparatus according to the invention in a bright place, it is preferable to provide a shielding means for shielding the forehead to prevent the same from being applied with foreign lights. The cup-shaped light emitter provides a merit to also achieve the function as the above shielding means. Shapes of the light emitter, particularly of the cup type, may be circular or transversely elliptical, but preferably longitudinally elliptical or in the form of upsidedown triangle for application of light to the forehead including its central part.

As electrodes for measuring brain waves, at least two electrodes such as an electrode for brain waves and that for grounding are required. Assembling positions of electrodes are not specifically limited, but the electrode for brain waves may be adapted to contact with the forehead, so that production of alpha waves (or alpha waves and theta waves) at the forehead are picked up more precisely and readily. In this case, since the electrode when adapted to contact with the central part of the forehead hinders application of pulsed light, it may be adapted to contact with the lateral part of forehead, i.e., temples or the area near the same. The grounding electrode is used usually by fitting to earlobes. An electrode for brain waves of a brain wave measuring device quite separate from the apparatus for applying pulsed light to forehead according to the present invention may be made use of in the invention. In this case, assembling such electrode in the fitting device is not required. But, in case the brain wave electrode is assembled in the fitting device, handling and operation are simple and easy. Assembling the brain wave electrode in the fitting device is essential particularly in the automatic adjustment type which causes the light-applying frequencies to correspond to a representative value of alpha waves (or alpha waves and theta waves, or theta waves) produced inherently by users.

The brain wave measuring electrode is connected with a brain wave indication means which indicates a representative value of frequencies in alpha wave range produced in brain of users. The brain wave indication means selects, by a filter (e.g., a bandpass filter 10 Hz), brain wave only in alpha wave range picked up from users, calculates average, center value, peak average, maximum value, etc., of the selected brain wave through arithmetic process, and indicates the values visibly by an electronic display tube or the like (digital or analog display), and vocally speaks out specific numerial values. Warning sounds may be produced for the case that average of user's inherent alpha wave and other values above deviates, more than a predetermined range (e.g., about 0.5 Hz), from a frequency set by user in use of the apparatus. The brain wave indication means when assembled directly in the fitting device is quite troublesome to use, particularly, in the visible type. Hence, the brain wave indication means may be provided separately from the main body (fitting device) to have communication therewith through transmission of signals with wire, radio or infrared or the like. The brain wave indication means making indication by sounds may be assembled in the main body, i.e., the fitting device in the headphone type and helmet type. The brain wave indication means is not essential for the aforesaid "automatic adjustment type" but may be provided to enable users to know the frequencies of their inherent alpha waves in use of the apparatus.

Next, the pulsed light frequency adjusting means will be detailed. The adjusting means is provided for enabling to apply a pulsed light of a frequency which is equal to or near a representative value of user's inherent alpha waves. The adjusting means has different structures for manual and automatic operation. For manual operation, the frequency adjusting means comprises a switch or dial for selecting any frequency equal to or near a representative value of inherent alpha wave shown by the brain wave indication means, and graduation showing frequencies. User sets a frequency for pulsed light to a representative value of their inherent alpha wave (e.g., shown with 0.1–0.2 Hz as a unit) visibly or audibly received by them. Since the operation when repeated frequently is troublesome and hinders relaxation and power of concentration, it is preferably to be carried out at intervals of from several minutes to dozens of minutes. The pulsed light frequency adjusting means in manual operation type may be separate from the main body (fitting device) to be readily and accurately operable. In such case, the adjusting means may be formed integrally with the aforesaid brain wave indication means and have communication with the main body through transmission of signals with wire, radio or infrared.

The pulsed light frequency adjusting means in automatic operation type performs operation in an electric circuit, thereby not requiring the control unit such as a switch, dial and graduation for frequencies. The electric circuit may employ any structures which amplifies user's brain wave signals picked up the brain wave measuring electrode, extracts only a signal component in the range of from 8 to 13 Hz corresponding to alpha wave through a filter to calculate a representative value of the signal component, and outputs a pulsed-light applying signal in the frequency range equal to or near the representative value. Among brain waves of users in sleep, theta waves (4–8 Hz) are more possibly prevalent in comparison with alpha waves (8–13 Hz), or it is largely possible that brain waves having lower alpha waves (8–9 Hz) together with theta waves are produced. Hence, the pulsed light frequency adjusting means particularly in the automatic adjustment type may be preferably adapted, in consideration of the stage in sleep, to extract signals in theta wave band or in the band of alpha waves with theta waves to calculate a representative value thereof. Also, a plurality of bandpass filters having differnt transmission frequencies may be provided to be switched for the respective stages of awareness and sleep of users.

Irrespective of manual or automatic operation, the light emitting means turns on and off according to photic stimulus signals corresponding the representative value of alpha wave (or alpha wave with theta wave), and applies the pulsed light to the forehead of users for stimulation. By this, brain waves produced by the user mostly become near that frequency range, so that relaxation and power of concentration are favourably maintained and further improved. The apparatus for applying pulsed light to forehead according to the present invention when used after relaxation or power of concentration is kept to some extent (about 5–20 min) provides a smooth induction of brain waves without harmful effects as causing users to feel ill. In view of such fact in the foregoing experiment results that when application of light and stoppage were repeated every 10 to 20 min, NK cell activity was occasionally seen also in the stoppage state, application of pulsed light may be carried out either continuously at a fixed time or in such manner that application and stoppage are repeated every suitable time. Control for this may be made mannually or automatically by use of a timer, etc.

The apparatus for applying pulsed light to forehead according to the present invention needs a control unit for processing signals and a power source for the control unit and the light emitting means, in addition to the above components. Those may be assembled in the main body (the fitting device) or formed integrally with the brain wave indication means and/or the frequency adjusting means.

The foregoing apparatus for applying pulsed light to forehead is used by fitting the apparatus itself to the head of users. The fitting procedure may be occasionally troublesome or the apparatus may disturb sleep of users. A desklamp type of the apparatus applying pulsed light to forehead may relieve users from the worries. This type of apparatus in use is fixed, for example, on an ordinary shelf or a shelf nearby a bed, or put on a desk, and adjusted in length and angles of an arm member to cause the pulsed light to be applied to the forehead of the user in sitting position or face-up position. In this case, the light emitting means may be modified in shape or an eye mask may be used to prevent pulsed light from going into the eyes. In reading at the desk with a strong light illuminating the desk surface, the pulsed light may be applied to the front side of the parietal region to allow user not to be irritated so much by reflection of the pulsed light on the desk surface.

The above two types of apparatus applying pulsed light to forehead are each provided with a light emitting means. The apparatus may include such means in place of the light emitting means as using sunlight or illuminating light for the pulsed light. This type of the apparatus comprises a fitting device provided with a shielding means for shielding user's forehead or the head including the forehead, and a shutter which is provided on an opening of the shielding means at the front side and intermittently shuts a light to be applied. In this case, frequencies of pulsed light are determined by the number of shutting/opening of shutter per unit time. The shutter may be structured mechanically or employ such feature electrically controlling clarity of a transparent member.

BRIEF DESCRIPTION OF THE DRAWINGS

FIG. 4(a) shows at the upper graph part a graph of prevalent brain wave appearance for one of testees at five frequency bands in Experiment B, at the middle graph part a graph showing transition of amplitude of brain waves at the five frequency ranges, and the lower graph part a graph showing transition of amplitude of brain waves only upon application of pulsed light, and FIG. 4(b) is the similar graph of the other testee.

FIG. 9(b) a graph for Experiment C-2 drafted under the same conditions as. FIG. 9(a), and FIG. 9(c) a graph for Experiment C-3 drafted under the same conditions as FIG. 9(a).

FIG. 18 is a perspective view showing an example of a desk-lamp type of apparatus for applying pulsed light to forehead in use.

FIG. 19 is a perspective view showing an example of an apparatus for applying pulsed light to forehead with intermittently shutting external light.

EMBODIMENTS

Figure 1A:
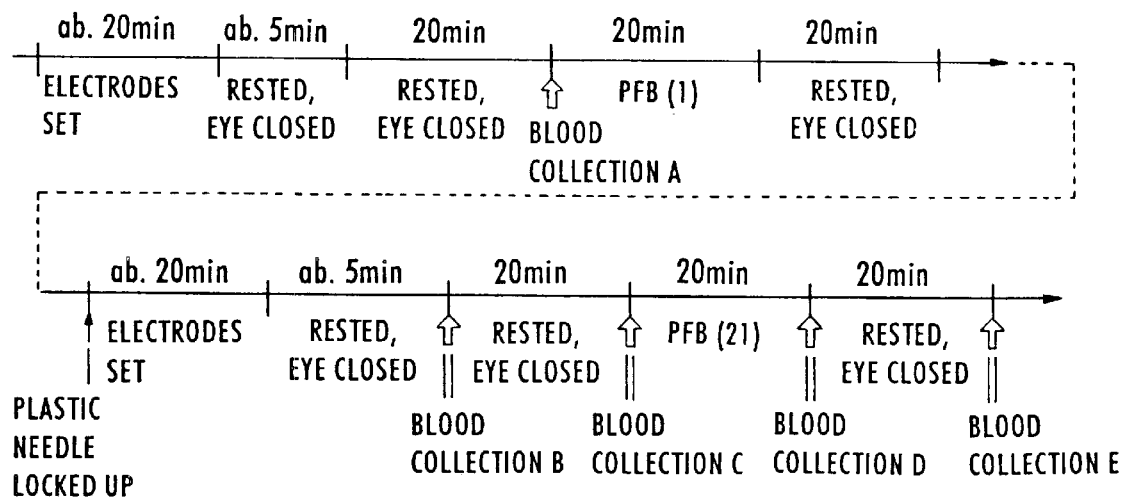
FIG. 1(a) is an explanatory view showing a procedure of PFB in Experiment A(a) applying pulsed light in front of the eyes not shielded against light, FIG. 1(b) a graph showing a change of NK cell activity in Experiment A(a), FIG. 1(c) a graph showing a change of NK cell activity in Experiment A(b) applying pulsed light to the forehead with the eyes not shielded against light, and FIG. 1(d) a graph showing average and dispersion (standard deviation) of the values of testees referred to FIG. 1(c).
Figure 1B:
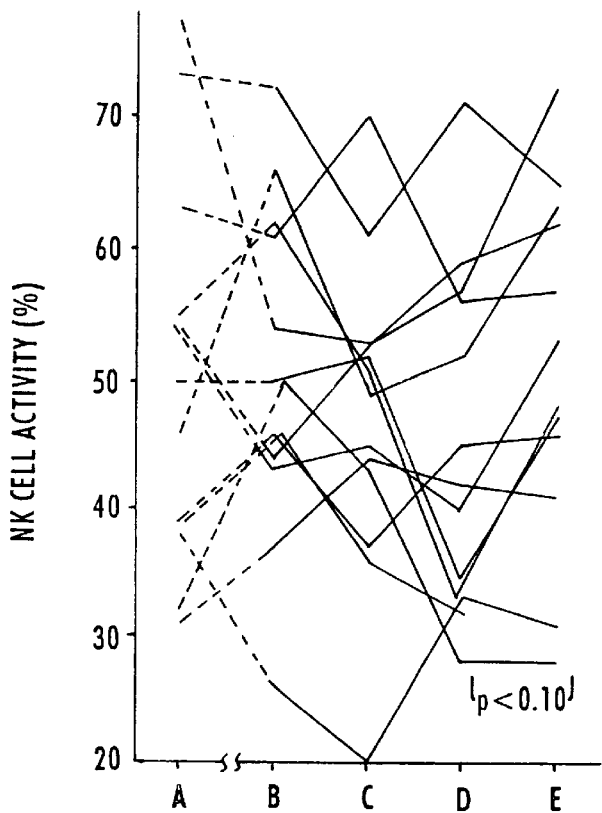
Figure 1C:
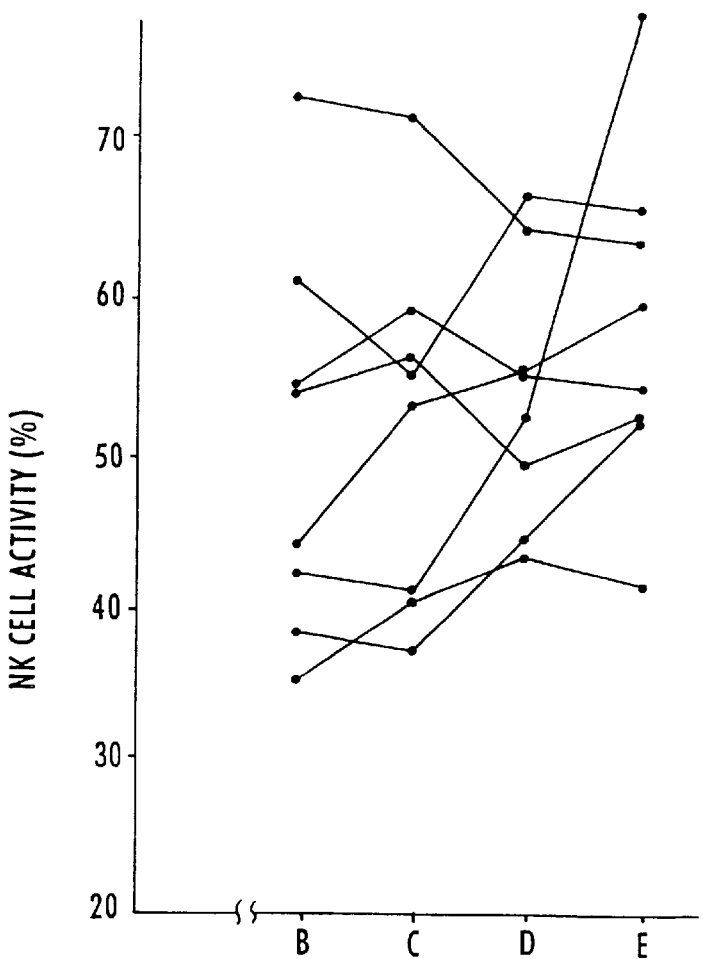
Figure 1D:
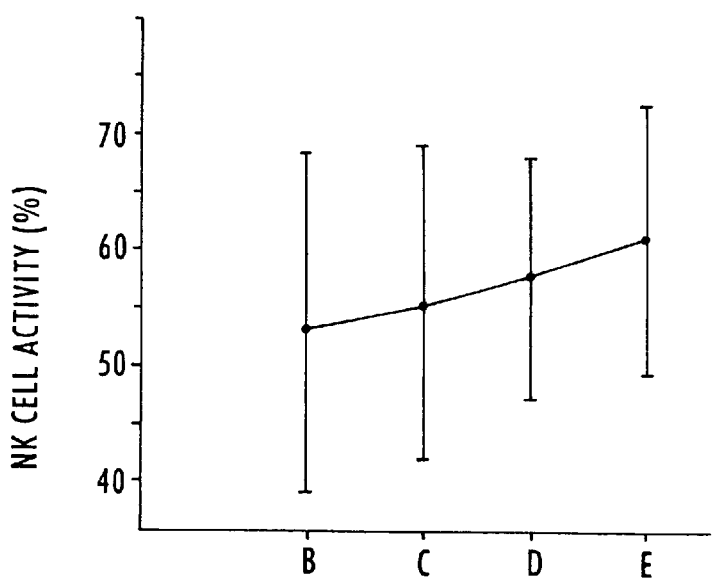
Figure 2A:
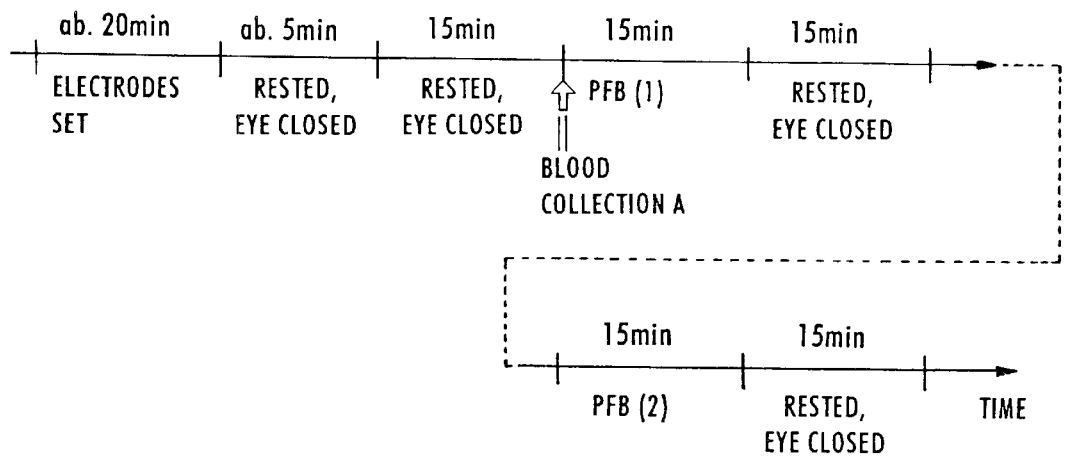
FIG. 2(a) is an explanatory view showing a procedure of 1st and 2nd PFB in Experiment B applying pulsed light to the forehead of testees with eyes being shielded with eye masks and one dish-type electrode being fit onto the right side part of forehead, and FIG. 2(b) a procedure of 21st, 22nd FFB drafted under the same conditions.
Figure 2B:
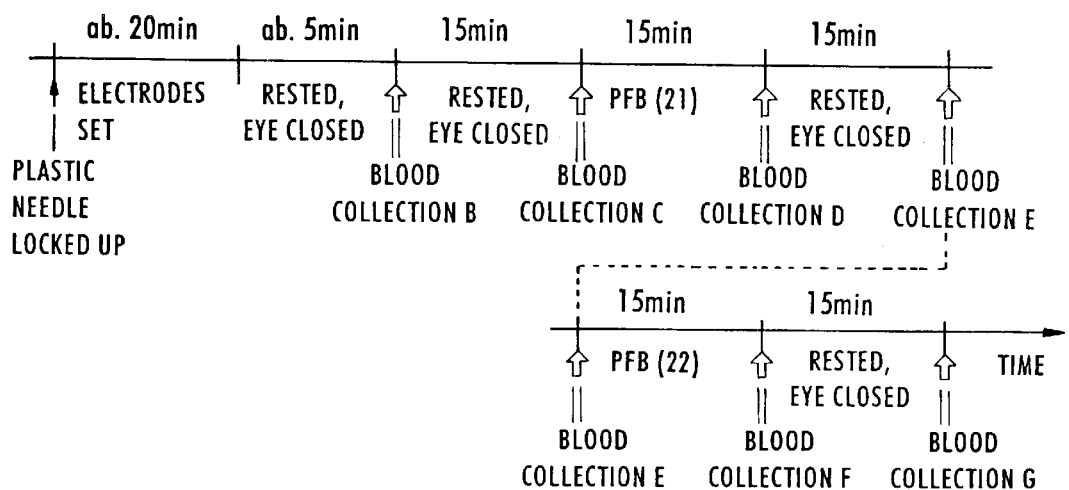
Figure 3:
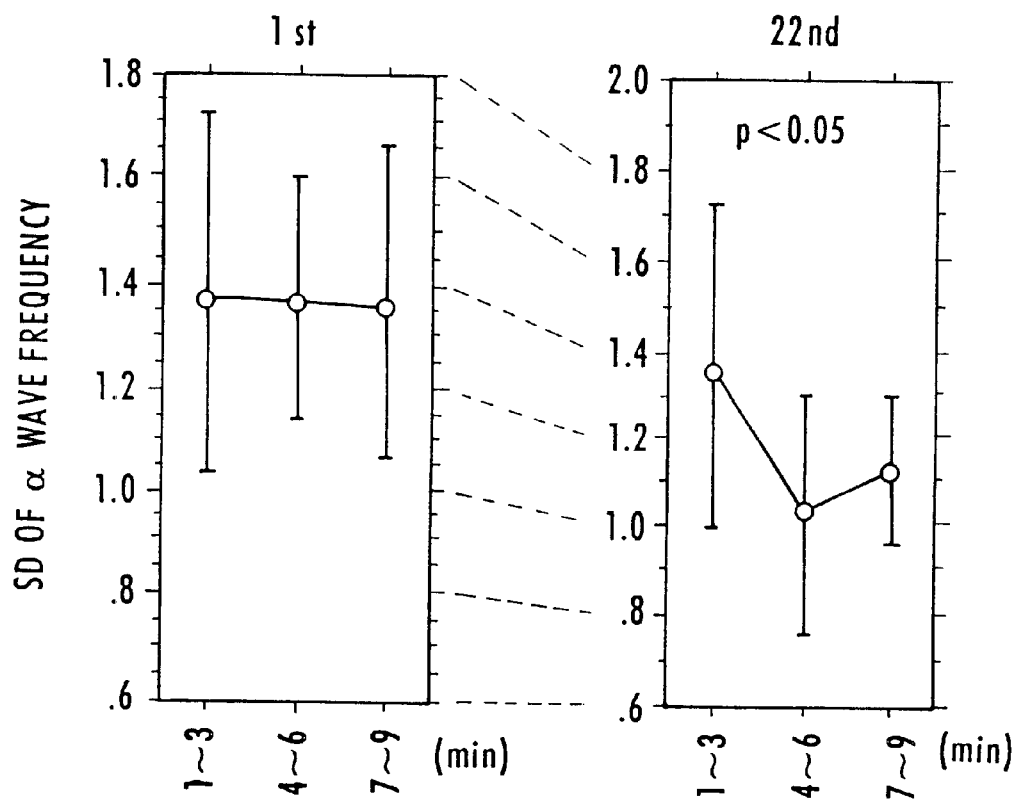
FIG. 3 is a graph showing transition of standard deviation (SD) of frequency of alpha wave detected at the right forehead ($Fp_2$) each three minutes three times until 9 min after start of 1st and 22nd PFB to the forehead in Experiment B. (n=7)
Figure 5A:
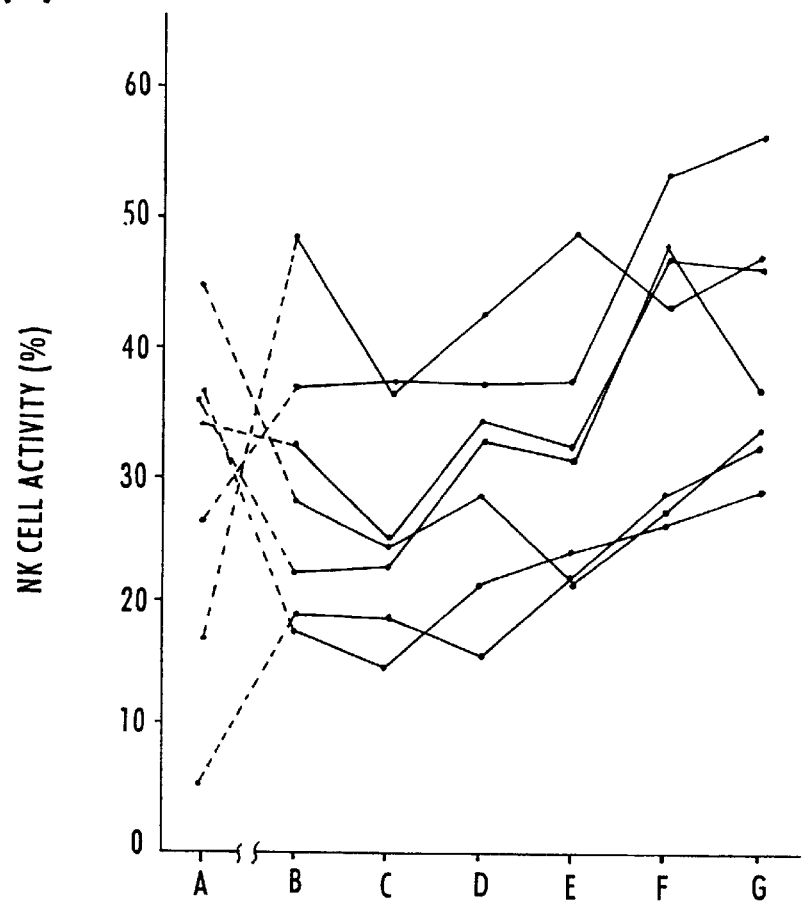
FIG. 5(a) is a graph showing a change of NK cell activity (%) in the testees at the stages before 1st PFB, during 21st, 22nd PFB and in the rested/eyes-closed states before and after the 21st,22nd PFB in Experiment B, and FIG. 5(b) average and dispersion (standard deviation) of NK cell activity in seven testees.
Figure 5B:
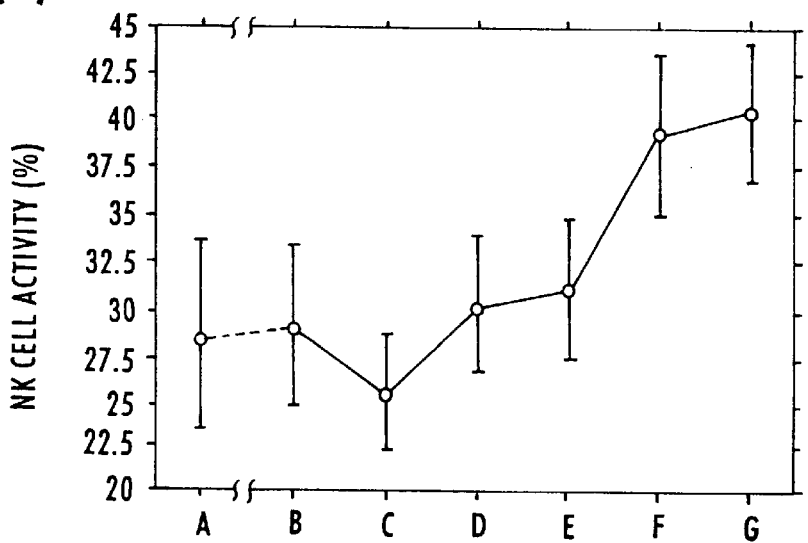
Figure 6:
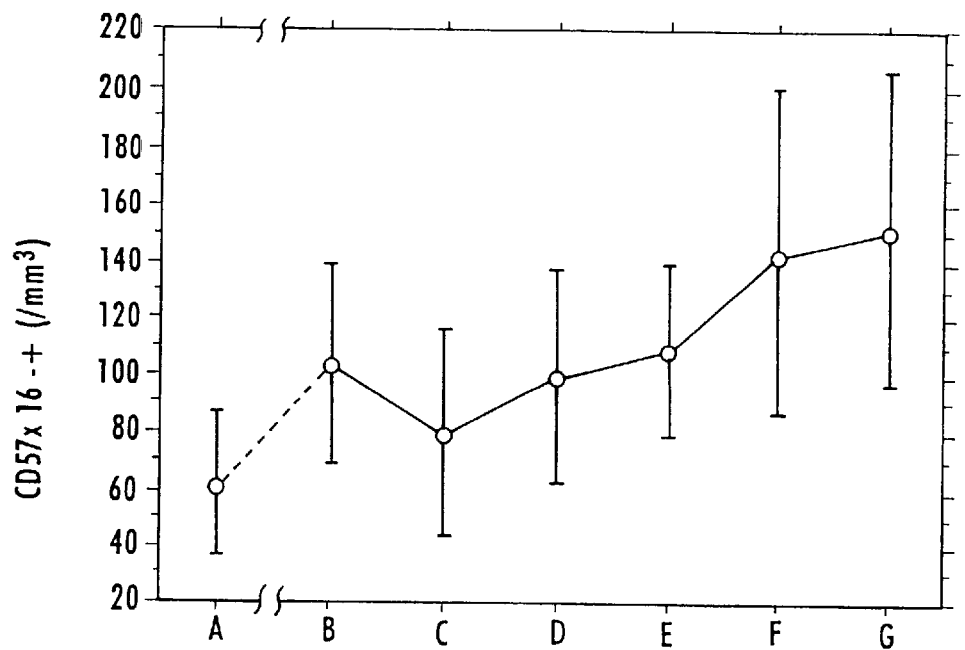
FIG. 6 is a graph showing a quantitative change of CD57×16++ at the stages immediately before 1st PFB, during 21st, 22nd PFB and in the rested/eyes-closed states before and after 21st, 22nd PFB in Experiment B.
Figure 7:
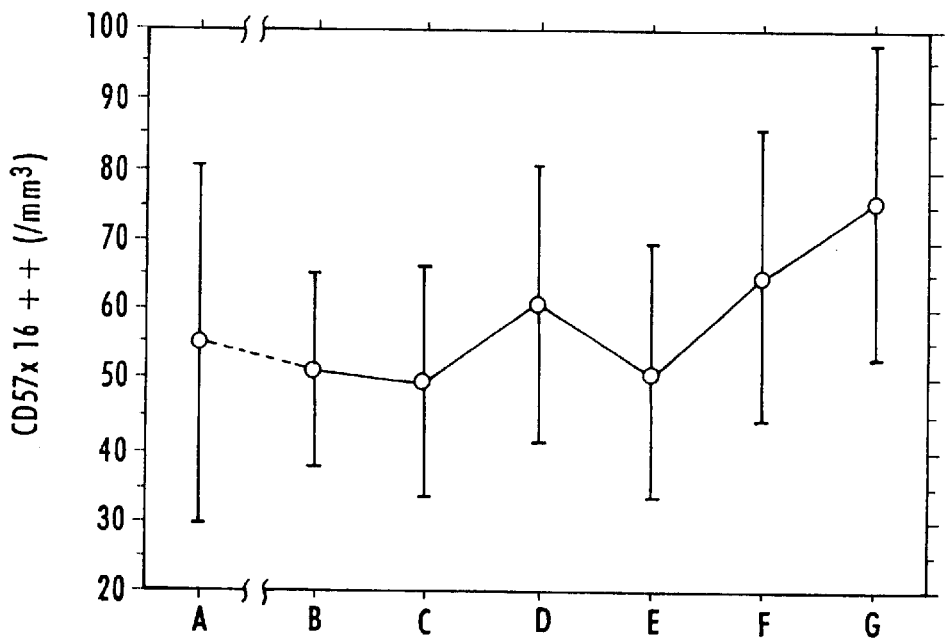
FIG. 7 is a graph showing a quantitative change of CD57×16−+ at the stages immediately before 1st PFB, during 21st, 22nd PFB and in the rested/eyes-closed states before and after 21st, 22nd PFB in Experiment B.
Figure 8A:
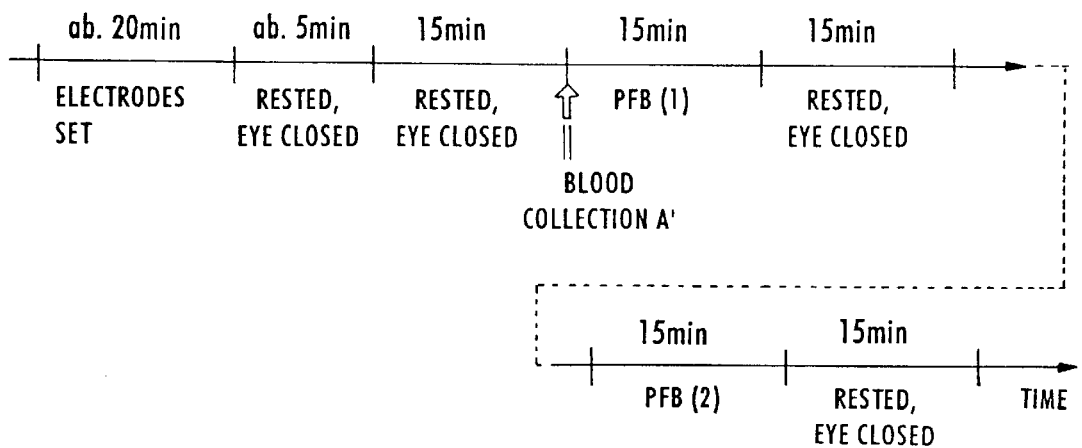
FIG. 8(a) is an explanatory view showing a procedure of 1st, 2nd PFB in Experiment C-1 with anti-light shielding not provided on the eyes of testee not yet operated.
Figure 8B:
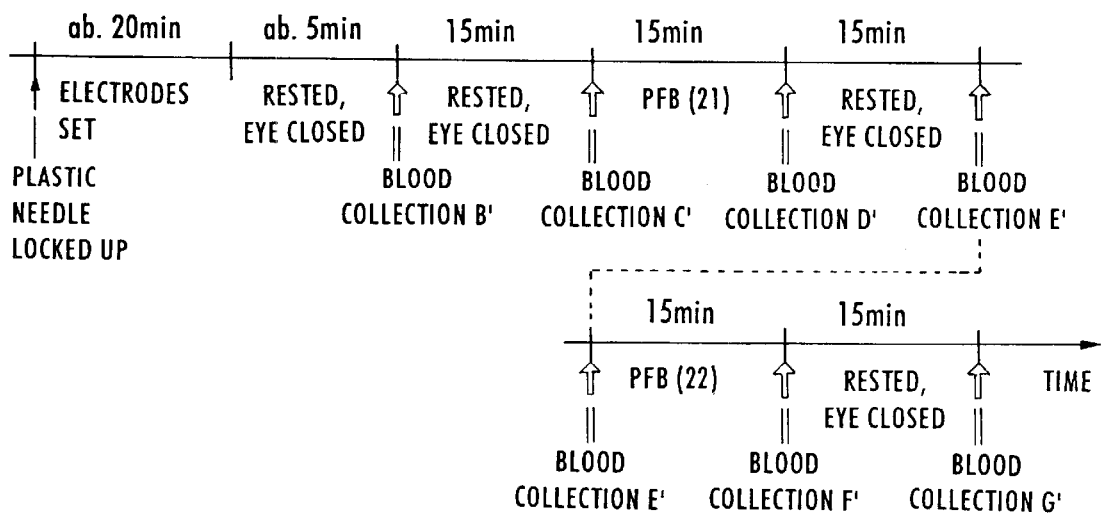
FIG. 8(b) an explanatory view showing a procedure of 21st, 22nd PFB drafted under the same conditions.
Figure 8C:
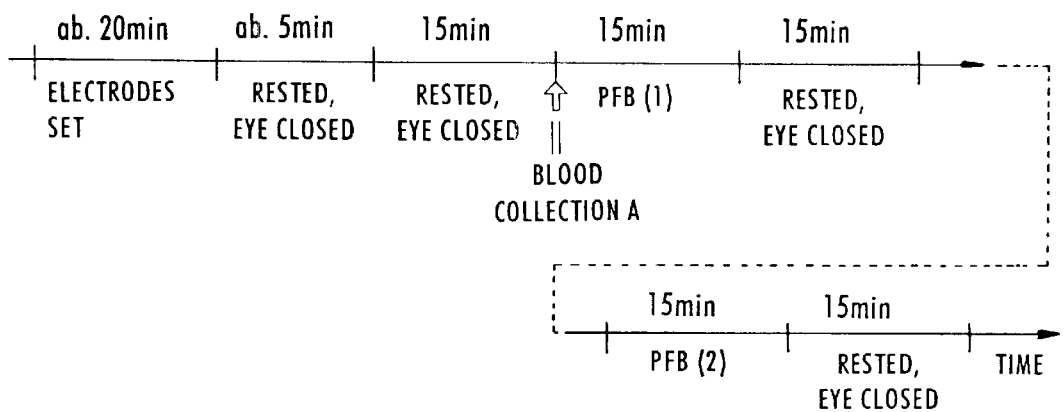
FIG. 8(c) an explanatory view showing a procedure of 1st, 2nd PFB in Experiment C-2 with anti-light shielding not provided on the eyes of testee already operated, FIG. 8(d) an explanatory view showing a procedure of 21st,22nd PFB drafted under the same conditions, and FIG. 8(e) an explanatory view showing a procedure of 21st, 22nd PFB in EXperiment C-3 with shielding provided on the eyes of testee already operated.
Figure 8D:
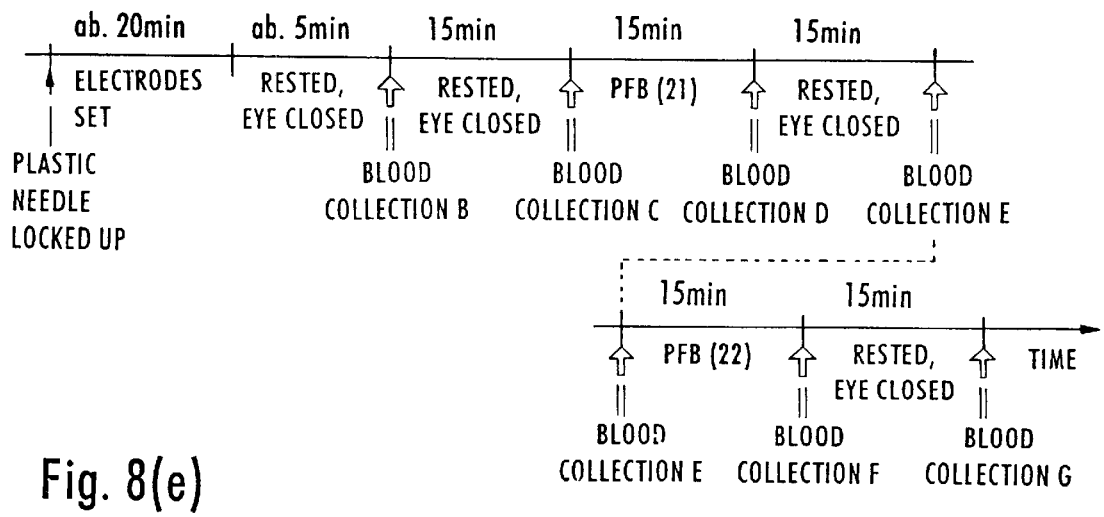
Figure 8E:
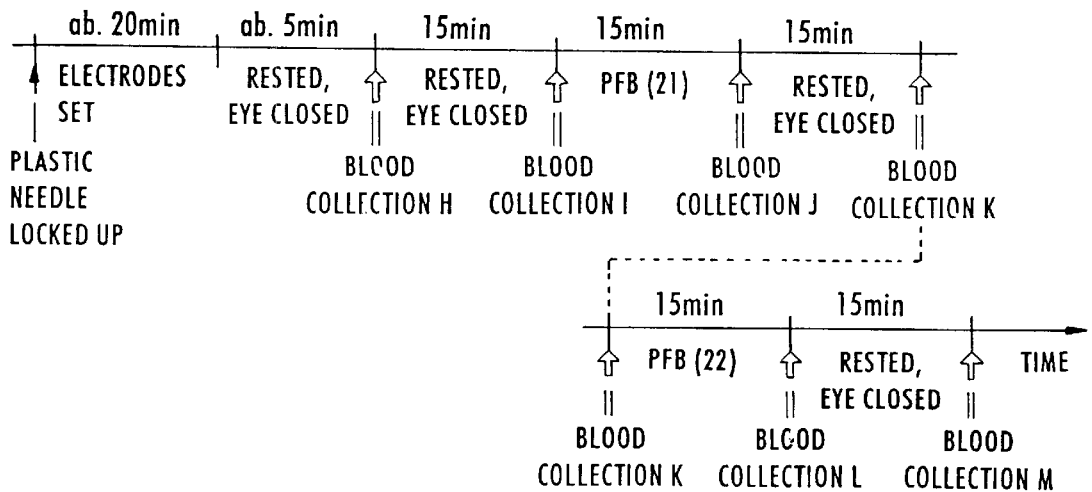
Figure 9A:
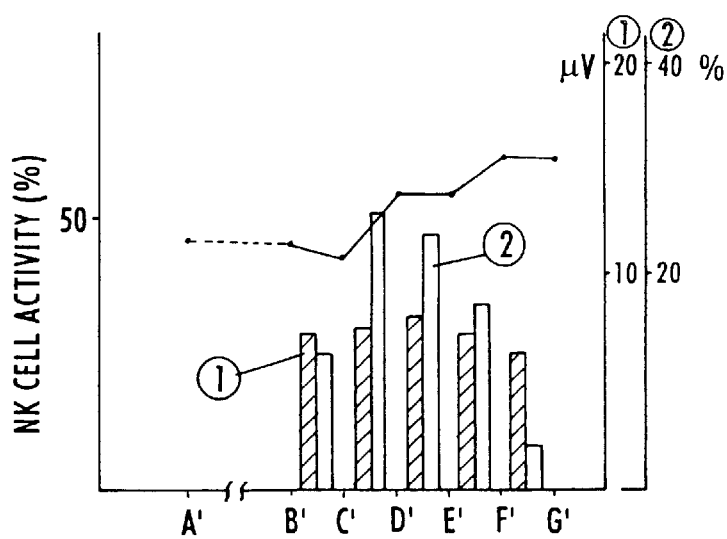
FIG. 9(a) is a graph showing a change of NK cell activity (by bent line), average of amplitude of produced $\alpha_3$ waves (hatched bar graph(1)), ratio of time when $\alpha_3$ wave was prevalent (hollow bar graph (2)) at the stages in 21st, 22nd PFB and in the rested/eyes-closed states before and after the PFB in Experiment C-1.
Figure 9B:
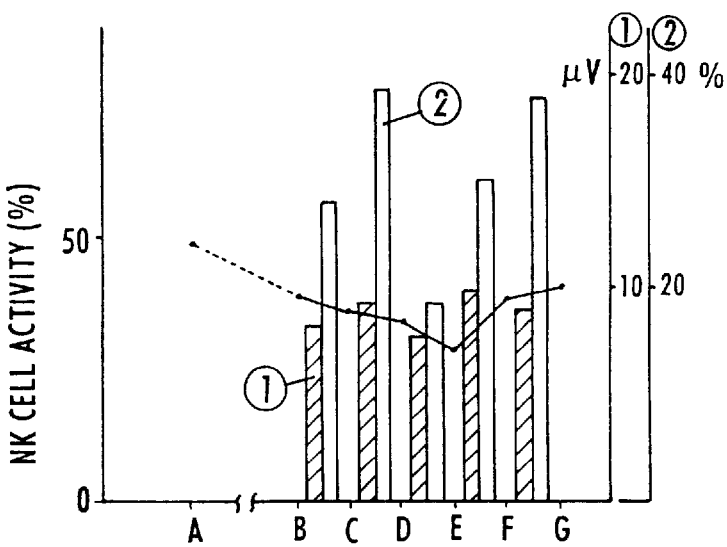
Figure 9C:
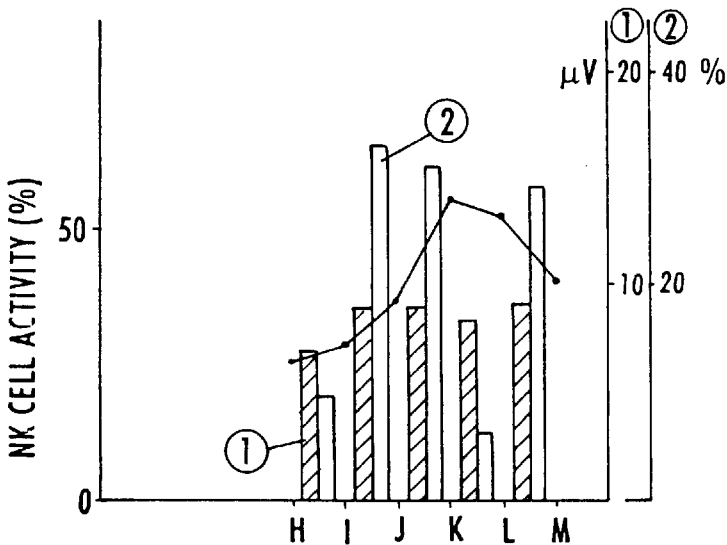

Next, the prevent invention will be detailed with referring to the examples shown in the drawings.

Figure 10A:
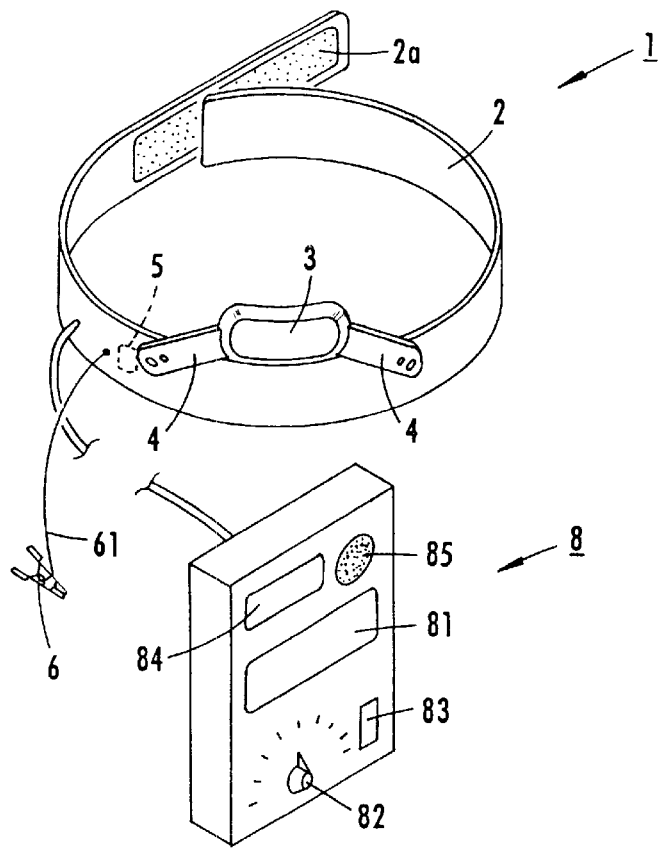
FIG. 10 shows an example of an apparatus for applying pulsed light to forehead according to the present invention, FIG. 10(a) being a perspective view, FIG. 10 (b) being a partially enlarged view showing a cross-section of an exemplary light emitter, and FIG. 10(c) a side view showing the apparatus fit onto the head of user.
Figure 10B:
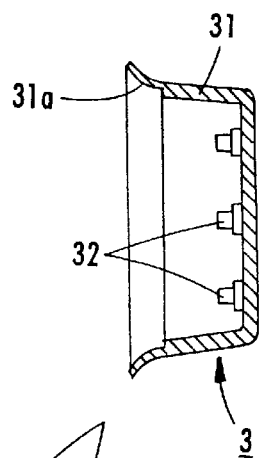
Figure 10C:
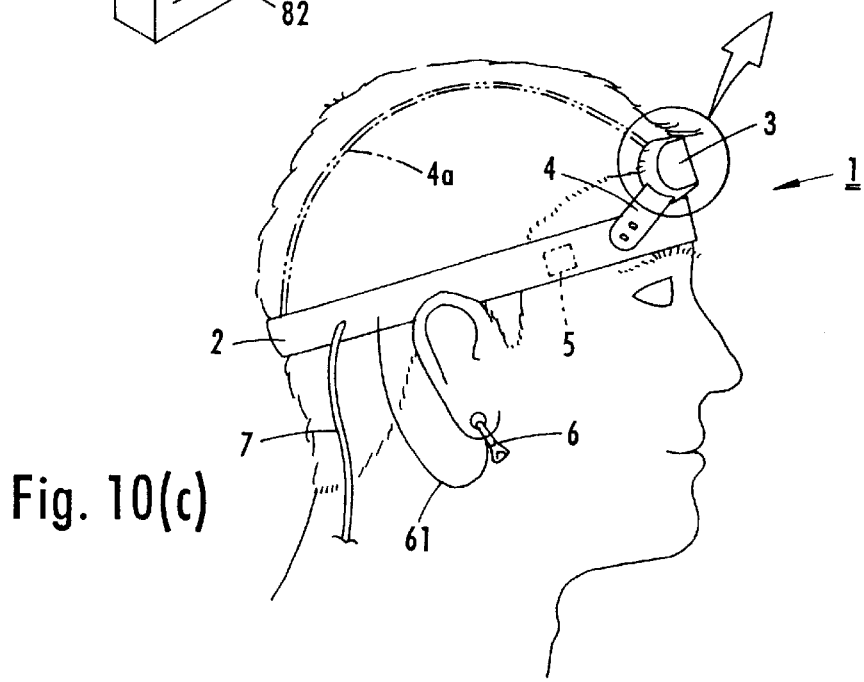

FIG. 10 shows an example of an apparatus for applying pulsed light to forehead according to the present invention, FIG. 10(a) being a perspective view and FIG. 10(c) a side view showing the apparatus fit on the head of user. The pulsed light applying apparatus 1 is in the belt type and comprises a band type fitting device 2 and an elliptical cup-like light emitting means 3 fixed at the front and upper part of the fitting device 2 through two support members 4. The fitting device 2 is adjustable in mounting length through an area fastener 2a. An electrode 5 for brain waves is fixed on the fitting device at its inner side near the part mounting the light emitting means 5. A grounding electrode 6 is mounted to the fitting device 2 through a code 61. The light emitting means 3 comprises, as seen in the partially enlarged FIG. 10(b), a light emitter 31 in an elliptic cup-like shape and a light source 32 fixed at the bottom of the light emitter 31. When the apparatus is fit onto the user's head as shown in FIG. 10(c), a front thinner edge 31a (shown in FIG. 10(b) of the light emitter 31 tightly fits to the forehead of user. Hence, the forehead is prevented from receiving foreign lights and the pulsed light is not applied to the eyes. The light emitting means 3 may be connected with the fitting device 2 by use of an auxiliary support member 4, as shown in FIG. 10(c) by the chain line, to allow the light emitting means 3 to further surely tightly fit onto the forehead.

Figure 11:
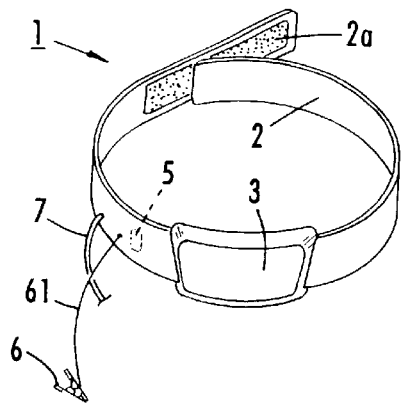
FIG. 11 is a perspective view showing another apparatus for applying pulsed light to forehead.

Alternatively, as seen in FIG. 11, the light emitting means 3 may mount a band serving as the fitting device 2 without use of the support member 4, thereby enabling application of pulsed light to the forehead including its central part. The effect is the same as of the feature shown in FIG. 13 described later. There is said such opinion that when the head is pressurized and stimulated, hair on the head is facilitated to grow. For this purpose, the band body of the band-type fitting device 2 shown in FIGS. 10 and 11 may be formed with a hollow member such as a tube in which air is injected. Furthermore, the apparatus for applying pulsed light to forehead 1 shown in FIG. 10 has a wire 7 extending from the fitting device 2 and having a control means 8 at the utmost end. The control means 8 comprises a brain wave indication means, frequency adjusting means, control panel and power source box and includes a brain wave display 81, frequency adjuster 82, switch 83, timer 84 and buzzer 85.

In use of the light-application apparatus 1, for relaxation, user first sits on a chair to rest for about from 5 to 20 min and then wears the apparatus on the head and turns on the switch 83. And for enhancing power of concentration, user first does intellectual activity such as reading, calculating, etc., for about from 5 to 20 min, and then, fits the apparatus on the head and turns on the switch 83. A representative value (average, etc) of alpha waves among brain waves picked up through the electrode 5 is then displayed on the brain wave diaplay 81. User reads the value and turns the dial to a corresponding frequency. By this, a pulsed light in the frequency range equal to or near the average of user's own alpha wave is applied from the light emitting means 3 to the forehead. When the application of pulsed light continued, the representative value having frequency of user's own alpha wave may happen to fluctuate. Hence, the representative value of user's own alpha wave may be displayed every predetermined time (e.g., several minutes to several dozens of minutes) to adjust the frequencies of pulsed light, providing further favourable effects. In this example, the control means 8 is connected to the fitting device 2 through the wire 7 but alternatively through radio or infrared to enable signals transmission therebetween and increase freedom upon operation. The timer 84 may be used to indicate time passed after start of use of the apparatus, and the buzzer for warning the case the inherent alpha wave deviates from the frequency of pulsed light, or for informing expiration of set time. The buzzer may be substituted with a speaker which indicates by sounds signals the information of instantenous state of user's inherent alpha waves.

Figure 12:
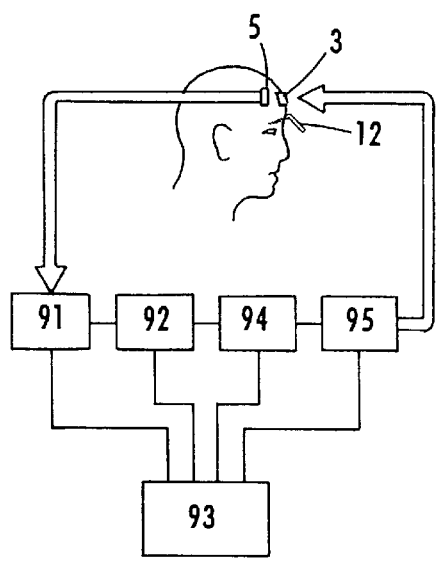
FIG. 12 is a schematic circuit diagram of a control unit used for automatic adjustment of frequencies of pulsed light.

FIG. 12 is a schematic diagram showing an example of a circuit 9 for control means used for the case of automatic adjustment of pulsed light frequencies, differing from the above example. First, brain waves picked up the electrode 5 is amplified by an amplifier 91, from which a filter 92 selects only those in alpha wave band, and a microcomputer 93 calculates average of thereof. Then, a level adjuster circuit 94 stabilizes outputs level, and a LED drive unit 95 performs voltage-current conversion to switch on the light source 32 at the light emitting means 3. An operating parts such as power source, switches, etc., are omitted from the drawing. Reference numeral 12 designates a shielding member for shielding the eyes from light.

Figure 13:
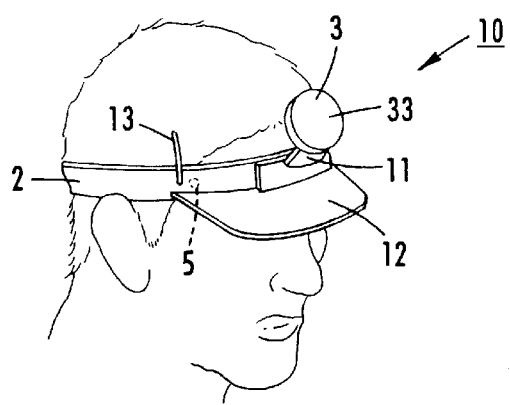
FIG. 13 is a perspective view showing still another apparatus for applying pulsed light to forehead, the apparatus being fit onto the head of user.

FIG. 13 shows another example of the belt-type of the apparatus applying pulsed light to forehead. The pulsed light-applying apparatus 10 comprises a band 2, two support members 11 and a light emitting means 3 supported by the band 2 and support members 11. The light emitting means 3 has a dish-like shaped light emitter 33. Thus, pulsed light is possibly applied also to the eyes. An eye-shielding member 12 is provided for preventing the eyes from being applied with the pulsed light. Reference numeral 13 designates an antenna which is connected, by radio, to a control means having the circuit exemplified in FIG. 12.

Figure 14:
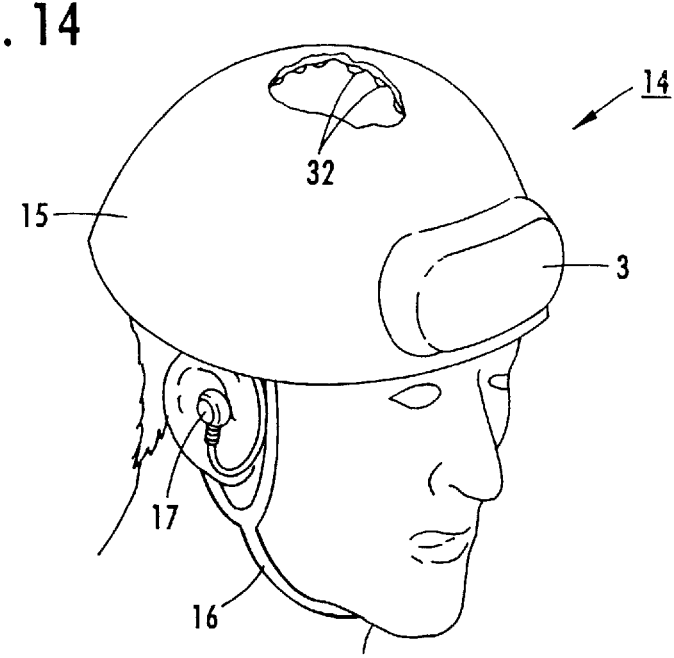
FIG. 14 is a perspective view showing still another apparatus for applying pulsed light to forehead, the apparatus being fit onto the head of user.

FIG. 14 shows an example of an apparatus for applying pulsed light to forehead comprising the fitting device in a cap (helmet) type. The pulsed light-appying apparatus 14 includes an elliptic cup-shaped light emitting means 3 assembled in the cap type fitting device 15 at its part corresponding to the user's forehead. The apparatus has a chin strap 16 for surely fitting the device on the head of user. Reference numeral 17 designates an earphone through which user listens to information of their instantaneous own alpha waves through sound signals. A light source emitting infrared, particularly, extreme infrared radiation may be assembled inside the cap-type fitting device 15 to stimulate scalp, enabling favourable effects for growing hair on the head. In this case, the cap-type fitting device 15 may be adapted to be worn deeply to enable the forehead to be applied with pulsed light in the slantwise upward direction, thereby eliminating provision of the light emitting means 3.

Figure 15:
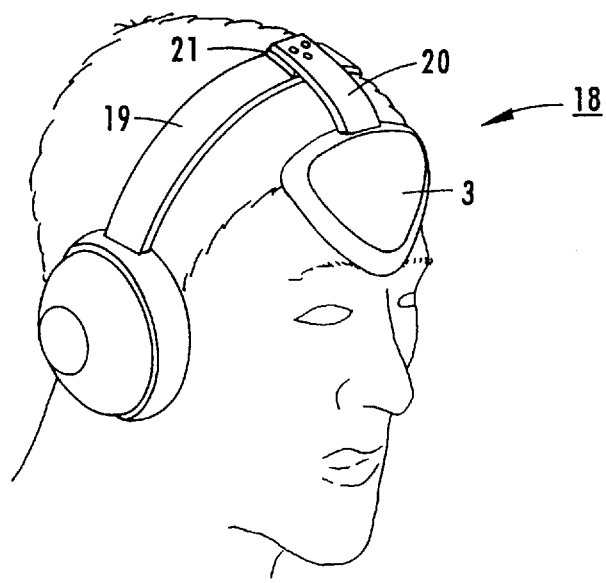
FIG. 15 is a perspective view showing still another apparatus for applying pulsed light to forehead, the apparatus being fit onto the head of user.

FIG. 15 shows an example of an apparatus for applying pulsed light to forehead provided with the fitting device in a headphone type. The light-applying apparatus 18 comprises the headphone type fitting device 19 which retains at the central part a support arm 20 at the free end of which a cup-shaped light emitting means 3 is mounted. The support arm 20 is adapted to push the forehead through a spring 21.

Figure 16A:
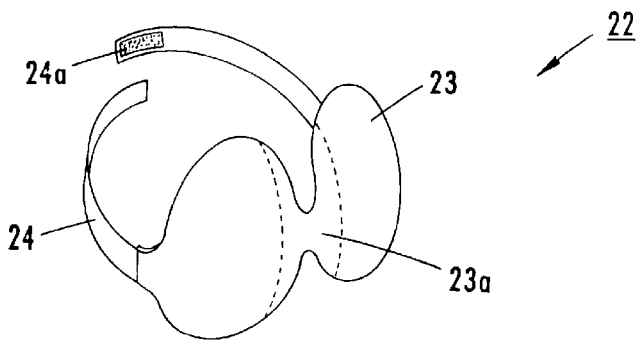
FIG. 16(a) is a perspective view of the state serving as the goggle and FIG. 16(b) a perspective view of the state serving as the apparatus for applying pulsed light to forehead.
Figure 16B:
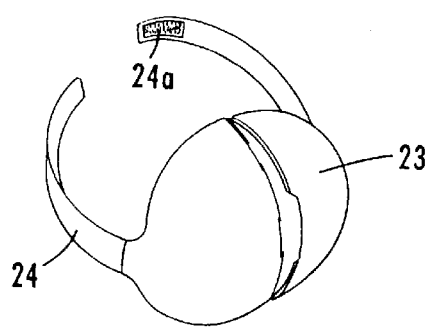
FIG. 16 shows an example of an apparatus for applying pulsed light to forehead serving also as a goggle for photic driving reaction.

FIG. 16 shows an example of an apparatus for applying pulsed light to forehead which also serves as a goggle for photic driving with respect to eyes. The light-applying apparatus 22 comprises an eye-mask 23 which is folded at the folding part 23a. The apparatus 22 when developed as seen in FIG. 16(a) provides a photic driving goggle, and becomes the apparatus for applying pulsed light to forehead when folded as in FIG. 16(b). Reference numeral 24 designates a band, and 24a an area fastener. Users may want to separately use enhancement of relaxation and power of concentration, and the apparatus in this example satisfies both of the purposes with the single apparatus.

Figure 17:
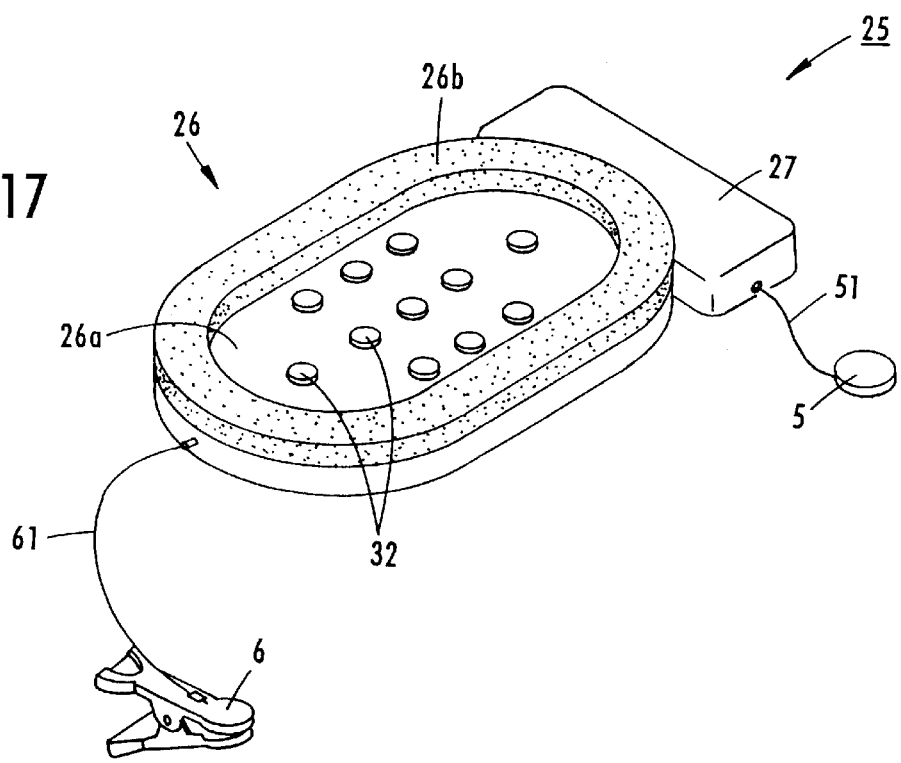
FIG. 17 is a perspective view showing another example of apparatus for applying pulsed light to forehead having a different fitting device.

FIG. 17 shows an example of an apparatus 25 for applying pulsed light to forehead having the fitting device different from those examples. The light-applying apparatus 25 comprises a fitting device which is made of a flexibile and adhesive retention member 26, and a light source 32 embedded in the retention member 26. The retention member 26 has a body 26a which has shading properties and is provided on its one surface with an adhesive layer 26b. The retention member 26 itself serves as a light emitting means 31. The retention member 26 are connected to brain wave electrode 5 and grounding electrode 6 through wires 51 and 61, respectively. Fitting of the apparatus 25 for applying pulsed light to forehead may be performed by adhering at and near the central part of forehead with the adhesive layer 26b. Measuring brain waves and control of pulsed light may be carried out by use of the control means 8 shown in FIG. 10(a). Alternatively, as shown, a control unit 27 including a pulsed light frequency adjusting means, power source, and control part each miniaturized may be integrally provided with the retention member 26 to make small and lightweight the whole apparatus 25 and cause users not to feel a sense of incongruity in sleep using the apparatus. Though not shown, the retention member 26 may employ a member having adsorption properties in place of the adhesive features. These type of fitting device allows the light source to be tightly fit onto the forehead, thereby enabling use of a light source even of less luminance.

FIG. 18 shows an example of a desk lamp type of apparatus 40 for applying pulsed light to forehead. The apparatus 40 comprises a base 41 having a fixing means 41a, a light emitting means 42 and a shiftale and deformable arm 43 connecting the base 41 and the light emitting means 43. The apparatus 40 is fixed at the base 41, for example, on a shelf 44 provided near a bed to apply pulsed light to the forehead of user in face-up position. The pulsed light is preferably to be applied in a form of a ring-like or semi-ring-like shape or of focused light of spotlight. Eye-masks 45 may be usable when required. Though not shown, the apparatus 40 in this example also may include the brain wave measuring electrode, brain wave inducing device, etc, or these devices may be separately provided and connected to one another by use of infrared or the like.

An apparatus 46 for applying pulsed light to forehead shown in FIG. 19 comprises a shielding means 47 for shielding the forehead or the head including the forehead, of users, a band 24 fixed to the shielding means 47, and a shutter 48 which is provided at an opening 47a on the front side of the shielding means 47 and intermittently shuts applied light from sunlight or an illuminating instrument without provision of the light emitting means 3. Reference numeral 24a designates an area fastener. The shutter 48 in this example comprises a frame plate 49 having slits 49a and a rotary disc 50 which is coupled therewith, has corresponding slits 50a and driven by a motor 51. The motor 51 may use a pulse motor to allow applied light to define excellent pulses. Frequencies of the pulsed light are determined depending upon the number and shapes of slits and number of revolutions of the rotary disc 50. Brain waves of users are measured, based on which the number of revolutions of the rotary disc 50 is controlled manually or automatically by a similar device to the foregoing pulsed light frequency adjusting means. Reference numeral 52 designates an extinction plate for preventing eyes from a strong sunlight. The extinction plate 52 may be opened and closed in the longitudinal direction. The extinction plate 52 may be substituted with a shading plate. Also, two rotary discs, in place of the frame plate 49 and a single rotary disc 50, may be employed to be rotated reversely to each other or in different number of revolutions from each other, by use of a pulse motor to enable the pulsed light to be applied uniformly on the forehead. The apparatus 46 in the example may be used to enable sunlight (which is said to be effective for health of human bodies) to be simply and surely applied as a pulsed light to the forehead of users. Though not shown, the apparatus 46 may include the brain wave measuring electrode and brain wave inducing device and others, or those devices may be separately provided to be connected to one another by use of infrared, etc.

EFFECTS OF THE INVENTION

As explained above, the method according to the present invention wherein pulsed light in the frequency range of 0.5–13 Hz is applied to the forehead or the head including the forehead with foreign lights being shielded, to enhance immunosurveillance capacity, particularly, NK cell activity, as well as power of concentration. Preferably, frequencies of pulsed light is set to a frequency equal to or near a representative value in the frequency range of alpha waves obtained by measuring brain waves of users, and application of pulsed light is carried out with the eyes of user being shielded against the pulsed light. As a result, the invention has the following various effects.

(1) Application of pulsed light with the eyes being shielded was carried out to enhance NK cell activity and increase alpha wave components at the forehead, thereby providing favourable relaxation and facilitation of power of concentration. However, in case pulsed light was applied also to eyes closed, alpha waves largely increased but NK cell activity did not show a significant increase.

(2) NK cell activity increased in a patient of cancer who being in administration of anti-cancer drug.

(3) Only application of pulsed light to the forehead or the head including the forehead is quite readily carried out and does not pain users, not at all cause them to feel anxious or uncomfortalbe and is a completely noninvasive method.

(4) Large effect of NK cell activity can be obtained to be significant in prevention of carcinogenesis and dislocation of cancer.

(5) NK cell activity can be improved without necessity of administration of medicines such as interferon, etc. And there are no production of resistance and no fear of adverse effect, differing from the conventional administration of medicines or immunotherapy.

(6) A safety process for about one hour provides a large increase of NK cell activity, more excellent than the various therapies and administration of medicines hitherto known.

(7) Noradrenaline decreases to provide an effective circumstance for immunosurveillance. In addition, adrenaline, dopamine, β-endorphin did not change, thereby having no adverse effect in this regard.

(8) The invention provides effects in sleep as well as in awareness to thereby be usable long.

(9) The invention does almost not take running cost and does not make users bear excessive expenses.

The apparatus for applying pulsed light to forehead comprises a light emitting means for applying pulsed light in the frequency range of alpha wave to the forehead or the head including the forehead of users, a pulsed light frequency adjusting means, a brain wave measuring electrode and a fitting device to be detachably fit onto the head of user. Hence, the invention provides the following various effects.

(1) The invention is simple in structure to be miniaturized and cheap to produce.

(2) The basic structures are a belt-type, cap or helmet type, headphone type, or retention member type through adhesion or adsorption. Thus, users do not feel uncomfortable when fitting the device on the head or forehead, and the device is readily usable.

(3) The retention member type may be subminiaturized to be favourably used in sleep. Also, the desk lamp type not fit on the head enables users to readily use the device in face-up position in sleep.

(4) The main body when separately provided from control means can be made lightweight. The main body when connected with the control means through radio or radiation has merit providing no troublesome usage.

(5) The invention provided with a brain wave inducing device in which a representative value of brain waves in user's own alpha wave band is obtained and fed back as a light-applying signal for pulsed light, does not cause brain of users to be extremely tired in a long use, but provides effects of maintenance and improvement of relaxation or intellectual concentration.

(6) The invention including the eye-shielding means does not cause pulsed light to be applied to the users eyes, thereby allowing users to maintain a complete relaxed state quite favourably.

(7) The invention having the eye-shielding means bears a continuous long time use and can be used with the users' eyes being opened while user is doing a separate activity.

(8) The invention having the eye-shielding means is usable while thinking, calculating or reading requiring power of concentration is continued. Hence, user's own alpha wave changes into alpha wave in a frequency range preferable for activating intellectual activities to thereby further increase power of concentration, which state is quite suitable for studying for entrance examination, etc.

(9) Operation is simple and sure as that user can manually adjust the frequencies of pulsed light while visibly or audibly observing average, etc of user's own alpha waves.

TABLE 1

| min | sec | β | α3 | α2 | α1 | θ |
|---|---|---|---|---|---|---|
| (a) | | | | | | |
| 2 | 46 | 43 | 41 | 53 | 34 | 41 |
| 2 | 48 | 36 | 40 | 47 | 68 | 39 |
| 2 | 50 | 31 | 38 | 42 | 61 | 48 |
| 2 | 52 | 34 | 37 | 36 | 40 | 34 |
| 2 | 54 | 32 | 40 | 66 | 47 | 34 |
| 2 | 56 | 27 | 34 | 43 | 34 | 43 |
| 2 | 58 | 38 | 59 | 67 | 54 | 45 |
| 3 | 0 | 56 | 157 | 198 | 93 | 66 |
| 3 | 2 | 69 | 200 | 200 | 103 | 73 |
| 3 | 4 | 83 | 200 | 200 | 112 | 80 |
| 3 | 6 | 59 | 200 | 200 | 93 | 62 |
| 3 | 8 | 58 | 200 | 193 | 99 | 59 |
| 3 | 10 | 67 | 200 | 182 | 126 | 97 |
| 3 | 12 | 81 | 200 | 200 | 135 | 93 |
| 3 | 14 | 60 | 200 | 200 | 103 | 87 |
| (b) | | | | | | |
| 10 | 16 | 48 | 85 | 200 | 161 | 64 |
| 10 | 18 | 44 | 81 | 200 | 163 | 58 |
| 10 | 20 | 65 | 96 | 200 | 195 | 87 |
| 10 | 22 | 44 | 91 | 200 | 178 | 77 |
| 10 | 24 | 46 | 83 | 200 | 145 | 74 |
| 10 | 26 | 43 | 85 | 200 | 168 | 90 |
| 10 | 28 | 50 | 82 | 200 | 200 | 132 |
| 10 | 30 | 41 | 91 | 200 | 137 | 69 |
| 10 | 32 | 38 | 84 | 200 | 101 | 55 |
| 10 | 34 | 56 | 83 | 200 | 200 | 74 |
| 10 | 36 | 45 | 98 | 200 | 152 | 75 |
| 10 | 38 | 47 | 103 | 200 | 144 | 67 |
| 10 | 40 | 42 | 62 | 159 | 189 | 76 |
| 10 | 42 | 54 | 80 | 200 | 123 | 98 |
| 10 | 44 | 58 | 91 | 200 | 188 | 74 |

TABLE 1-continued

| | (c) | |
|---|---|---|
| | max | av. |
| β | 20.8 | 12.1 |
| α3 | 50.0 | 25.3 |
| α2 | 50.0 | 49.6 |
| α1 | 50.0 | 40.4 |
| θ | 36.0 | 19.1 |

TABLE 2

| min | sec | β | α3 | α2 | α1 | θ |
|---|---|---|---|---|---|---|
| (a) | | | | | | |
| 2 | 46 | 56 | 52 | 60 | 41 | 34 |
| 2 | 48 | 57 | 53 | 58 | 54 | 42 |
| 2 | 50 | 61 | 46 | 44 | 40 | 37 |
| 2 | 52 | 50 | 58 | 85 | 42 | 34 |
| 2 | 54 | 44 | 49 | 49 | 38 | 31 |
| 2 | 56 | 55 | 46 | 52 | 38 | 38 |
| 2 | 58 | 61 | 63 | 58 | 38 | 36 |
| 3 | 0 | 69 | 169 | 154 | 66 | 37 |
| 3 | 2 | 42 | 192 | 97 | 51 | 43 |
| 3 | 4 | 33 | 122 | 120 | 49 | 39 |
| 3 | 6 | 38 | 149 | 114 | 53 | 38 |
| 3 | 8 | 31 | 126 | 83 | 50 | 41 |
| 3 | 10 | 30 | 89 | 78 | 43 | 34 |
| 3 | 12 | 53 | 156 | 122 | 62 | 36 |
| 3 | 14 | 34 | 90 | 67 | 55 | 36 |
| (b) | | | | | | |
| 10 | 16 | 40 | 59 | 179 | 49 | 35 |
| 10 | 18 | 66 | 103 | 200 | 86 | 49 |
| 10 | 20 | 35 | 68 | 200 | 57 | 51 |
| 10 | 22 | 40 | 69 | 200 | 61 | 38 |
| 10 | 24 | 71 | 97 | 200 | 90 | 56 |
| 10 | 26 | 53 | 67 | 200 | 121 | 51 |
| 10 | 28 | 29 | 62 | 200 | 55 | 52 |
| 10 | 30 | 28 | 60 | 148 | 44 | 34 |
| 10 | 32 | 37 | 55 | 139 | 49 | 33 |
| 10 | 34 | 77 | 92 | 200 | 150 | 58 |
| 10 | 36 | 38 | 59 | 131 | 65 | 39 |
| 10 | 38 | 83 | 108 | 200 | 103 | 51 |
| 10 | 40 | 43 | 66 | 200 | 95 | 50 |
| 10 | 42 | 62 | 98 | 200 | 81 | 52 |
| 10 | 44 | 53 | 85 | 185 | 80 | 40 |

| | (c) | |
|---|---|---|
| | max | av. |
| β | 32.5 | 11.5 |
| α3 | 48.0 | 18.9 |
| α2 | 50.0 | 42.0 |
| α1 | 50.0 | 20.5 |
| θ | 24.8 | 11.6 |

TABLE 3

| | Average difference | Degree of Freedom | t values | p values |
|---|---|---|---|---|
| A, B | −.614 | 6 | −.086 | .9341 |
| A, C | 2.929 | 6 | .456 | .6642 |
| A, D | −1.800 | 6 | −.317 | .7623 |
| A, E | −2.743 | 6 | −.390 | .7101 |
| A, F | −10.743 | 6 | −1.599 | .1608 |
| A, G | −11.957 | 6 | −1.777 | .1259 |
| B, C | 3.543 | 6 | 1.982 | .0948 |
| B, D | −1.186 | 6 | −.588 | .5780 |
| B, E | −2.129 | 6 | −1.095 | .3157 |
| B, F | −10.129 | 6 | −2.571 | .0423 |

TABLE 3-continued

| | Average difference | Degree of Freedom | t values | p values |
|---|---|---|---|---|
| B, G | −11.343 | 6 | −4.312 | .0050 |
| C, D | −4.729 | 6 | −2.612 | .0400 |
| C, E | −5.671 | 6 | −2.723 | .0345 |
| C, F | −13.671 | 6 | −4.564 | .0038 |
| C, G | −14.886 | 6 | −9.151 | <.0001 |
| D, E | −.943 | 6 | −.512 | .6267 |
| D, F | −8.943 | 6 | −3.275 | .0169 |
| D, G | −10.157 | 6 | −4.329 | .0049 |
| E, F | −8.000 | 6 | −2.591 | .0412 |
| E, G | −9.214 | 6 | −3.596 | .0114 |
| F, G | −1.214 | 6 | −.593 | .5748 |

TABLE 4

| | Average difference | Degree of Freedom | t values | p values |
|---|---|---|---|---|
| A, B | −41.714 | 6 | −2.531 | .0446 |
| A, C | −18.286 | 6 | −1.239 | .2616 |
| A, D | −37.857 | 6 | −2.553 | .0433 |
| A, E | −48.286 | 6 | −5.069 | .0023 |
| A, F | −82.143 | 6 | −5.722 | .0012 |
| A, G | −91.571 | 6 | −6.608 | .0006 |
| B, C | 23.429 | 6 | 3.284 | .0167 |
| B, D | 3.857 | 6 | .325 | .7559 |
| B, E | −6.571 | 6 | −.492 | .6402 |
| B, F | −40.429 | 6 | −1.603 | .1600 |
| B, G | −49.857 | 6 | −2.358 | .0564 |
| C, D | −19.571 | 6 | −3.249 | .0175 |
| C, E | −30.000 | 6 | −3.248 | .0175 |
| C, F | −63.857 | 6 | −3.007 | .0238 |
| C, G | −73.286 | 6 | −4.296 | .0051 |
| D, E | −10.429 | 6 | −1.208 | .2725 |
| D, F | −44.286 | 6 | −2.254 | .0650 |
| D, G | −53.714 | 6 | −3.122 | .0205 |
| E, F | −33.857 | 6 | −2.105 | .0799 |
| E, G | −43.286 | 6 | −3.696 | .0101 |
| F, G | −9.429 | 6 | −.925 | .3908 |

TABLE 5

| | Average difference | Degree of Freedom | t values | p values |
|---|---|---|---|---|
| A, B | 3.714 | 6 | .270 | .7959 |
| A, C | 5.429 | 6 | .412 | .6946 |
| A, D | −5.714 | 6 | −.503 | .6328 |
| A, E | 4.143 | 6 | .579 | .5834 |
| A, F | −9.857 | 6 | −1.872 | .1104 |
| A, G | −20.000 | 6 | −3.232 | .0179 |
| B, C | 1.714 | 6 | .265 | .7995 |
| B, D | −9.429 | 6 | −1.319 | .2352 |
| B, E | .429 | 6 | .048 | .9635 |
| B, F | −13.571 | 6 | −1.105 | .3114 |
| B, G | −23.714 | 6 | −2.298 | .0612 |
| C, D | −11.143 | 6 | −1.164 | .2886 |
| C, E | −1.286 | 6 | −.133 | .8985 |
| C, F | −15.286 | 6 | 1.550 | .1722 |
| C, G | −25.429 | 6 | −2.182 | .0719 |
| D, E | 9.857 | 6 | 1.295 | .2430 |
| D, F | −4.143 | 6 | −.389 | .7104 |
| D, G | −14.286 | 6 | −1.863 | .1117 |
| E, F | −14.000 | 6 | −1.862 | .1119 |
| E, G | −24.143 | 6 | −4.154 | .0060 |
| F, G | −10.143 | 6 | −1.189 | .2793 |

I claim:

1. An apparatus for applying pulsed light to a user's forehead comprising a fitting device adapted to be detachably fit onto the head of a user and provided with a shielding member which shields the forehead or the head including the forehead of the user and is provided on an opening at the front side with a shutter for intermittently shutting a light applied to the forehead or the head including the forehead of the user, and also comprising brain wave measuring electrodes and a brain wave inducing device which picks up a signal component in the range of α wave among brain wave signals of the user from the brain wave measuring electrodes and calculates a representative value of the signal component, and feeds back the representative value or any frequency near the same as a shutter control signal.

2. An apparatus for applying pulsed light to a user's forehead comprising a fitting device adapted to be detachably fit onto the head of a user and provided with a shielding member which shields the forehead or the head including the forehead of the user and is provided on an opening at the front side with a shutter for intermittently shutting a light, said apparatus being configured so that said light is applied to the forehead or the head including the forehead of the user when the fitting device is fit onto the head of the user, wherein said shutter is configured to intermittently shut all light applied to said opening.

3. An apparatus for applying pulsed light to a user's forehead comprising a fitting device adapted to be detachably fit onto the head of a user and provided with a shielding member which shields the forehead or the head including the forehead of the user and is provided on an opening at the front side with a shutter for intermittently shutting a light, said apparatus being configured so that said light is applied to the forehead or the head including the forehead of the user when the fitting device is fit onto the head of the user, wherein said shutter comprises a rotary disc having at least one slit therein for transmitting light therethrough.

4. The apparatus of claim 3, wherein said shutter further comprises a frame plate having at least one slit corresponding to said at least one slit of said rotary disc.

5. The apparatus of claim 1, 2 or 4, wherein there is provided integrally a brain wave measuring means having electrodes for measuring brain waves.

6. The apparatus of claim 1, 2 or 4, further including an eye-shield for blocking light into the user's eyes.

7. The apparatus of claim 1, 2 or 4, further including an eye-shade for shading light into the user's eyes.

8. The apparatus of claim 1, 2 or 4, wherein said apparatus is configured so that said opening is located above the user's eyes when the fitting device is fit onto the head of the user.

9. The apparatus of claim 8, wherein said shutter intermittently shuts light applied through said opening.

* * * * *